(12) United States Patent
Ryu

(10) Patent No.: US 8,010,186 B1
(45) Date of Patent: Aug. 30, 2011

(54) SYSTEM AND RELATED METHODS FOR IDENTIFYING A FIBRILLATION DRIVER

(75) Inventor: Kyungmoo Ryu, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 594 days.

(21) Appl. No.: 11/458,655

(22) Filed: Jul. 19, 2006

(51) Int. Cl.
*A61B 5/04* (2006.01)

(52) U.S. Cl. ......................................................... 600/509

(58) Field of Classification Search .................. 600/515, 600/518; 607/122; 606/34, 41
See application file for complete search history.

(56) References Cited

U.S. PATENT DOCUMENTS

| | | | |
|---|---|---|---|
| 5,238,007 A * | 8/1993 | Giele et al. .................... | 607/126 |
| 5,305,202 A * | 4/1994 | Gallant et al. ................. | 600/524 |
| 5,772,604 A * | 6/1998 | Langberg et al. ............. | 600/518 |
| 5,954,665 A * | 9/1999 | Ben-Haim ..................... | 600/515 |
| 5,991,657 A | 11/1999 | Kim | |
| 6,041,251 A | 3/2000 | Kim et al. | |
| 6,298,257 B1 * | 10/2001 | Hall et al. ...................... | 600/407 |
| 6,496,731 B1 | 12/2002 | Lovett | |
| 6,519,490 B1 * | 2/2003 | Wiesel .......................... | 600/518 |
| 6,584,343 B1 * | 6/2003 | Ransbury et al. ............. | 600/509 |
| 2002/0188214 A1 * | 12/2002 | Misczynski et al. .......... | 600/516 |
| 2002/0193838 A1 | 12/2002 | Lovett | |
| 2004/0059237 A1 * | 3/2004 | Narayan et al. ............... | 600/509 |
| 2005/0080347 A1 | 4/2005 | Sheth et al. | |

FOREIGN PATENT DOCUMENTS

| | | |
|---|---|---|
| EP | 1021222 B1 | 10/2004 |
| WO | WO0001299 | 1/2000 |
| WO | WO0007663 | 2/2000 |
| WO | WO2004026123 A2 | 4/2004 |
| WO | WO2004026123 A3 | 4/2004 |

* cited by examiner

*Primary Examiner* — Carl H Layno
*Assistant Examiner* — Allen Porter, Jr.

(57) ABSTRACT

A system and related methods for assisting a user approximate the location of a fibrillation driver within a heart. The system includes an electrode and a computer, which is coupled to the electrode. The electrode is configured to sense a signal emitted from a location in the heart. The computer is configured to calculate a standard deviation of cycle length value for the signal. The user can approximate the location of the fibrillation driver based on a comparison of the standard deviation of cycle length value to other standard deviation of cycle length values that previously have been calculated by the computer for signals emitted from other locations in the heart.

14 Claims, 14 Drawing Sheets

SYSTEM AND RELATED METHODS FOR IDENTIFYING A FIBRILLATION DRIVER

FIELD OF THE INVENTION

The invention relates to the field of systems and related methods for locating a source of fibrillation in a heart. More specifically, the invention relates to a system and related methods for locating a source of fibrillation in the heart based on cardiac cycle length measurements.

BACKGROUND OF THE INVENTION

Atrial fibrillation ("AF") is a common example of an atrial tachyarrhythmia, which is characterized by having a fast atrial rate and a variable ventricular rate. In AF, the regular electrical impulses that are generated by the heart's sinoatrial ("SA") node are interfered with, or replaced, by other less regular and more rapid reentrant electrical impulses. Thus, AF results in irregular heart beats. Typically, AF is not life threatening, however, the likelihood of stroke is increased in individuals that experience AF.

In order for AF to exist, the surface area of the atria must be relatively large and contiguous. Surgical procedures that subdivide the conducting tissue of the atria can eliminate AF. An example of one such procedure is the Maze procedure, in which the atria are surgically segmented during an open-heart surgical procedure so that reentrant electrical signals can not propagate through the atria. During the Maze procedure, a surgeon creates a series of linear incisions in the surface of the atria, resulting in a mazelike pattern of scars. The surgically created scars electrically subdivide the atria in such a manner that AF can not be supported.

Other procedures for eliminating AF involve the use of an ablation catheter. The ablation catheter is inserted into a patient's heart, typically, via the patient's venous system, e.g., through the patient's jugular vein, without the need for open-heart surgery. During one type of ablation procedure, a medical practitioner moves the ablation catheter until the distal end of the ablation catheter, which includes an ablation electrode, contacts heart tissue that is to be ablated. Next, the medical practitioner applies energy, e.g., radiofrequency ("RF") energy or microwave energy, to the ablation electrode, which, in turn, creates thermal energy at the distal end, which scars the heart tissue. In other types of ablation catheters, the distal end includes a piezoelectric crystal that is configured to transmit ultrasound energy into heart tissue that contacts the distal end. The transmission of ultrasound energy into the heart tissue creates thermal energy, which scars the tissue.

Typically, the ablation energy heats the heart tissue to a temperature ranging from approximately 65° C. to approximately 100° C. for between 10 to 60 seconds. By moving the ablation catheter's distal end while applying thermal energy to the heart tissue, the medical practitioner creates linear scars in the heart's tissue, which subdivide the surface area of the atria in a manner similar to that of the Maze procedure. In practice, the effectiveness of the scars created using the ablation catheter approximate the effectiveness of the scars created during a Maze procedure.

In another ablation procedure, the ablation catheter is used to destroy only a limited region of the heart's tissue. More specifically, in an effort to control the rate of the heart, the atrioventricular ("AV") node is ablated and a pacemaker, which controls the rate of the patient's heart rate, is implanted. In other ablation techniques, one or more cells, also referred to as "focal points" are ablated. Typically, these focal points are located in the left atrium near the pulmonary vein, and believed to be the origination point for AF. These focal points, as well as reentrant circuits, in the heart are referred to as "drivers." The drivers are referred to as "AF drivers" when the drivers initiate AF. These AF drivers can provide a single, stable electrical activation that drives an atrium for a very short cycle length, e.g., a cycle length on the order of approximately 100 milliseconds to approximately 200 milliseconds.

Ablation techniques are most successful when the ablation energy is delivered to the heart's tissue in an accurate manner. Currently, the medical practitioner may map the response of the heart to an applied stimulus in an effort to accurately determine the location for the delivery of the ablation energy. During this mapping procedure, the ablation electrode can be used to electrically stimulate various locations in the heart. The medical practitioner compares the resulting electrocardiogram ("ECG"), which is detected using external electrodes, to intracardiac signals detected using the ablation electrode.

If the ablation electrode is co-located with the AF driver, the ECG and intracardiac signals detected after stimulation will match the ECG and intracardiac signals that result during an AF event. In this manner, the medical practitioner can determine whether the ablation electrode is co-located with the AF driver by carefully comparing the ECGs and the intracardiac signals that result from the mapping procedure as the ablation electrode is moved along the interior surface of the heart. This comparison of the ECGs and intracardiac signals can be tedious and time-consuming for the medical practitioner because the differences in the timing and shape of the ECG and intracardiac signals can be subtle. After the medical practitioner determines that the ablation electrode is co-located with the AF driver, the medical practitioner will prompt the ablation electrode to transmit energy into the heart tissue that contacts the ablation electrode in an effort to destroy the driver.

Another technique for treating AF involves the use of implantable medical devices ("IMDs"), e.g., pacemakers, cardioverters, and/or defibrillators, which are surgically implanted into a patient and configured to sense the occurrence an AF event. Also, the IMDs are configured to deliver pacing therapy and/or shock therapy to the atria via lead electrodes that are coupled to an IMD in an effort to treat the AF event and to restore normal cardiac rhythm. The ability of the IMD to regulate an AF event and the amount of electrical energy required from the IMD to regulate an AF event is dependent upon how close one of the IMD's lead electrodes is positioned relative to the AF driver.

Accordingly, during the IMD implantation process, every effort must be made by the medical practitioner to co-locate the lead electrode with the AF driver. Similar to the previously mentioned ablation procedure, the medical practitioner will attempt to co-locate the lead electrode with the AF driver by comparing ECG signals and intracardiac signals sensed by the lead electrode, as the lead electrode is moved along the interior surface of the heart. It can be difficult for a medical practitioner to co-locate the IMD's lead electrode with the AF driver because the comparison of the electrical signal waveforms can be time-consuming and tedious for the medical practitioner.

It should, therefore, be appreciated that there is a need for a system and a related method for assisting a medical practitioner to quickly and accurately determine the location within a patient's heart where ablation energy should be delivered, or where an IMD lead electrode should be located, during therapeutic procedures associated with the elimination of fibrillation. The present invention satisfies these needs, as well as others as discussed below.

SUMMARY

Embodiments described herein include a system and methods for assisting a user, e.g., a medical practitioner, to quickly and accurately locate the position for the application of ablation energy and/or where an IMD lead electrode is to be located during procedures that are associated with the elimination of fibrillation. An exemplary embodiment is a system that is configured to assist the user approximate the location of a fibrillation driver within a heart. The system includes plural electrodes and a computer, which is coupled to the electrodes. The electrodes are configured to sense signals emitted from respective locations in the heart. The computer is configured to calculate standard deviations of cycle length value for the signals. The approximate location of the driver is based on a comparison of the standard deviations of cycle length value.

An exemplary method for determining an approximate location of a fibrillation driver within a heart includes using plural electrodes to sense signals emitted from various locations within the heart, communicating the signals from the electrodes to the computer, using the computer to calculate standard deviations of cycle length value for the signals, and comparing the standard deviations to determine the approximate location of the fibrillation driver within the heart based on a result of the comparison of the standard deviation of cycle length value and the other standard deviation of cycle length values.

Other features of the invention should become apparent from the following description of the preferred embodiments taken in conjunction with the accompanying drawings, which illustrate, by way of example, the principles of the invention.

DETAILED DESCRIPTION OF THE PREFERRED EMBODIMENTS

Embodiments of the present invention advantageously provide a user, e.g., a medical practitioner, with the capability of quickly and accurately determining the location of a driver in a patient's heart. In particular, embodiments of the present invention facilitate the timely and accurate placement of an ablation catheter or an IMD lead electrode, near the location of the driver. As a result, the overall surgical time can be reduced and the efficiency of the therapeutic procedure can be enhanced.

Figure 1:
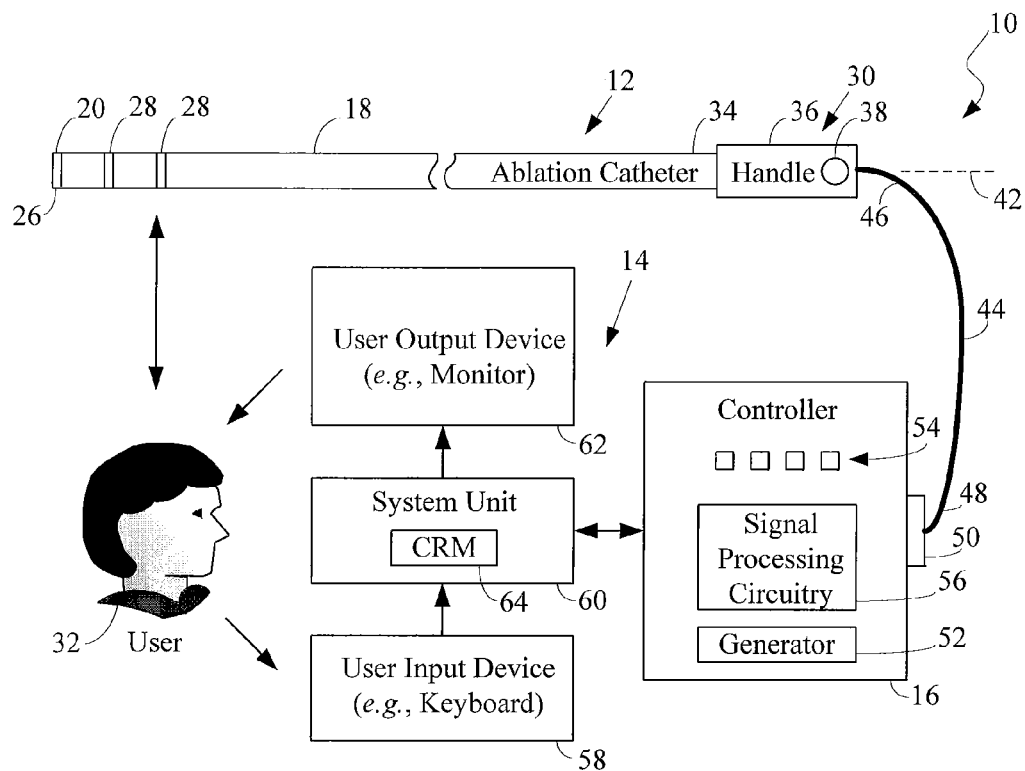
FIG. 1 is a simplified block diagram of an ablation system according to an embodiment of the present invention.

FIG. 1 is a simplified illustration of a system 10 that is used for heart ablation therapy. The system includes an ablation catheter 12, a computer 14, and a controller 16, which is coupled between the ablation catheter and the computer. The ablation catheter includes a thin flexible tube 18 made of, for example, silicone and/or polyurethane. Typically, the ablation catheter has a diameter ranging from approximately 5 French to approximately 8 French, and a length of approximately 100 centimeters to approximately 130 centimeters in length.

Figure 2:
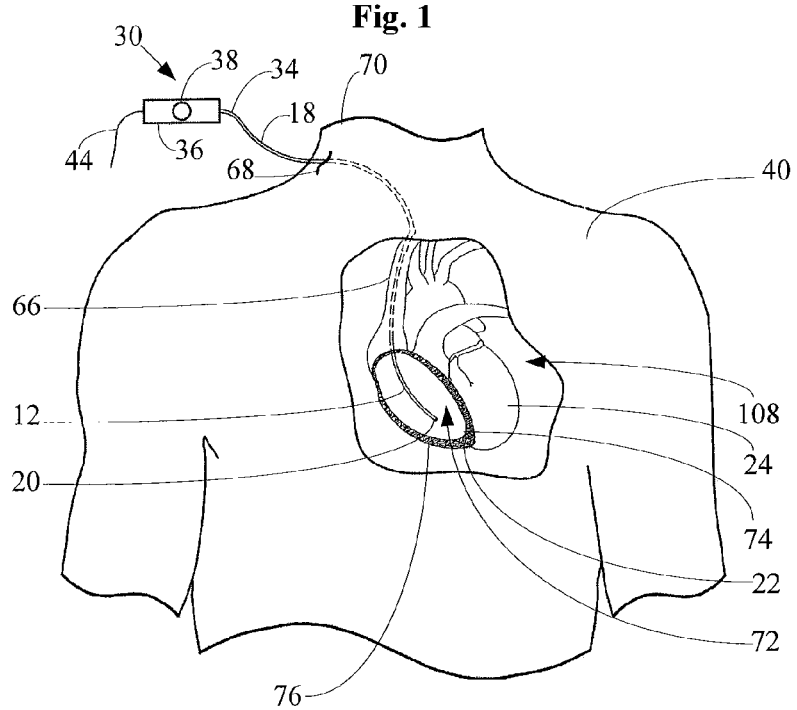
FIG. 2 is a partial cross-sectional front view of a patient's body with an ablation catheter inserted into the patient's heart.

Referring additionally to FIG. 2, the ablation catheter 12 has a distal end 20, which is configured to contact the tissue 22 of the heart 24 and to transmit ablation energy into the contacted tissue. The transmission of ablation energy into the heart tissue can be accomplished in several different ways. For example, the ablation catheter's distal end can include an ablation electrode 26, which is configured to transmit electrical energy into the heart tissue. In the case where the ablation catheter includes an ablation electrode at its distal end, the ablation electrode also is configured to emit electrical signals that can be used to stimulate the tissue of the heart that is in contact with the distal end.

In another example, the distal end 20 of the ablation catheter 12 includes a piezoelectric crystal (not shown) that is configured to generate ultrasound energy that is transmitted into the heart tissue 22. In yet another example, the distal end of the ablation catheter cryogenically transmits thermal energy into the heart tissue. The ablation catheter also can include additional sensors, e.g., additional electrodes 28 and/or thermal sensors (not shown), which can be used to sense the heart's tissue. For example, the ablation catheter can include one or more band electrodes 28, which can be used to sense intracardiac electrical signals, near the distal end of the ablation catheter.

Typically, the ablation catheter 12 includes a steering mechanism 30, which allows a medical practitioner 32 to move the distal end 20 and/or to impart a desired curvature to the distal end. The steering mechanism usually includes one or more wires (not shown), which are located within the ablation catheter. The wires couple the distal end to the other end of the ablation catheter, i.e., the proximal end 34, where the wires connect to a handle 36. The handle can include, for example, a switch (not shown) or a dial 38 that is configured to be manipulated by the medical practitioner to move the wires, which, in turn, maneuver the distal end.

In most ablation catheters 12, the distal end 20 has a preformed curvature or shape, and the force that the medical practitioner 32 applies to the wires (not shown) via the handle 36, enables the ablation catheter's distal end to return to its preformed curvature or shape. Thus, the steering mechanism 30 provides for the dynamic adjustment of the ablation catheter's contour during use. For example, the ablation catheter can be straightened during insertion or removal of the catheter from the patient 40, and curved after the distal end is positioned within the heart 24.

The medical practitioner 32 also can use the handle 36 to rotate the ablation catheter 12 about its axis 42. Accordingly, because of the ability of the medical practitioner to move the distal end 20 via the steering mechanism 30, and the ability of the medical practitioner to rotate the ablation catheter about its axis, the medical practitioner can move the distal end of the ablation catheter in three dimensions.

Also, the ablation catheter 12 includes an interface cable 44 having one end 46 that couples to the handle, and another end 48 that couples to a connector 50. The connector is configured to be coupled to the controller 16. When the interface cable is coupled to the controller, the interface cable allows for the propagation of ablation energy from the controller to the ablation electrode 26, and the transmission of electrical signals sensed by the ablation catheter's electrodes 26 and 28 to the controller via wires (not shown) internal to the ablation catheter.

The controller 16 includes an energy generator 52, which is configured to provide the ablation catheter 12 with the energy, e.g., RF energy, microwave energy, or ultrasonic energy, that is to be used during the ablation procedure. The type and the amount of energy that is output from the controller's energy generator to the ablation catheter can be controlled by the medical practitioner 32 via the controller, i.e., the medical practitioner uses the controller in a self-controlled mode of operation. In other embodiments, the type and amount of energy that is output from the controller to the ablation catheter can be controller using the computer 14.

The controller 16 includes buttons 54 that provide a user interface for operating the controller, e.g., turning on and off the ablation energy, selecting the ablation temperature, and/or selecting the amount of power to use during the ablation procedure. Also, the controller includes signal processing circuitry 56, which is configured to receive the intracardiac signals that are sensed by the ablation catheter's electrode(s) 26 and 28 and to process, e.g., amplify, the intracardiac signals before they are transmitted to the computer 14 for analysis.

The computer 14, e.g., a personal computer, is configured to control the operation of the controller 16 and/or to analyze the intracardiac signals sense by the ablation catheter's electrode(s) 26 and 28. The computer can receive input and control information from the medical practitioner 32 via a user input device 58, e.g., a keyboard, a writing interface, and/or a voice interface. Through the user input device, the medical practitioner can issue commands via the computer's system unit 60, i.e., the computer hardware that includes the computer's central processing unit, to the controller that control the operation of the controller and the ablation catheter 12. The computer also includes a user output device 62, e.g., a monitor and/or a printer, which is configured to display information related to the status of the controller and/or the ablation catheter, and/or data collected from the ablation catheter's electrode(s) or other sensor(s). In addition, the computer includes the appropriate software for manipulating and analyzing the information received from the ablation catheter and/or the controller. The software is stored in a computer-readable medium ("CRM" in FIG. 1) 64, e.g., a RAM, a ROM, an EEPROM, a flash memory, a CDROM, a DVD, an optical disk, a magnetic cassette, a magnetic tape, a magnetic disk drive, or any other medium that can be used to store information. The computer-readable medium can be included in the computer, or coupled to the computer.

The ablation catheter 12 is configured to be inserted into a patient's venous system 66 through a small incision 68. Typically, the incision is made in the patient's neck 70 or groin (not shown), and the ablation catheter is inserted into the patient's jugular vein (not shown) or femoral vein (not shown), respectively. During the insertion process, the medical practitioner 32 pushes the distal end 20 of the ablation catheter through the patient's venous system and into one or more of the chambers 72 of the patient's heart. Once the distal end of the ablation catheter is located within the heart, the medical practitioner uses the handle 36 of the ablation catheter's steering mechanism 30 to direct the distal end into contact with the tissue 22 of the heart 24, and the ablation catheter is used to ablate the inside layer, i.e., the endocardial layer 74, of the heart. Also, the ablation catheter can be inserted into the patient 40 via a hole (not shown) in the pericardium (not shown), and can be used to ablate heart tissue in the outside layer, i.e., the epicardial layer 76, of the heart.

Typically, before ablation energy is applied to the heart tissue 22, the medical practitioner 32 will manipulate the ablation catheter 12 so that the distal end 20 touches various locations within or on the heart 24 during electrophysiological ("EP") mapping procedures, which allow the medical practitioner to determine the types of arrhythmias experienced by the patient 40, to induce arrhythmias in the patient's heart for diagnostic purposes, and to locate sites of poor conduction that might trigger arrhythmia. At these locations, an electrode 26, or electrodes 26 and 28, included in the ablation catheter is used to sense intracardiac signals, which ultimately are communicated to the computer 14 where the intracardiac signals are analyzed. Referring additionally to the right-hand side of FIG. 3, the intracardiac signals can be displayed on the user output device 62 as waveforms 78, e.g., time-domain waveforms, for viewing by the medical practitioner. The medical practitioner will decide where the ablation energy should be applied to the heart depending upon his or her analysis of the waveforms.

Figure 4:
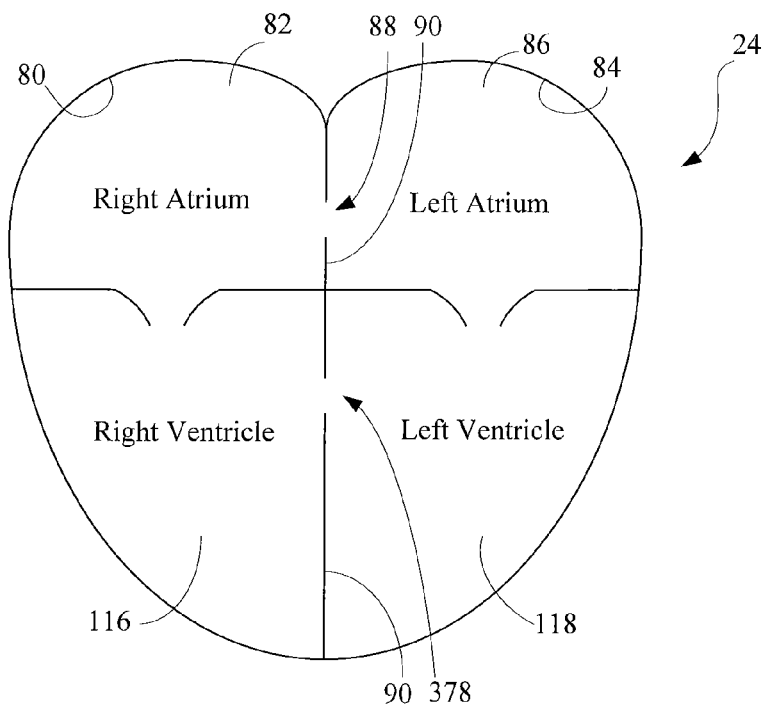
FIG. 4 is a simplified illustration of the patient's heart.

Referring additionally to FIG. 4, the medical practitioner 32 can use the above procedure to map the interior surface 80 of the right atrium 82, the interior surface 84 of the left atrium 86, or both using the ablation catheter 12. Before the left atrium is mapped, the medical practitioner will create a hole 88 through the septum 90 between the right atrium and left atrium using a transseptal technique known to those individuals having ordinary skill in the art. Next, the medical practitioner will insert the distal end 20 of the ablation catheter from the right atrium into the left atrium through the hole. After the distal end of the ablation catheter is inserted into the left atrium, the medical practitioner will maneuver the distal end of the ablation catheter into contact with the tissue 22 of the left atrium for mapping purposes. After the ablation procedure is completed, the hole will self-heal over time.

Figure 5:
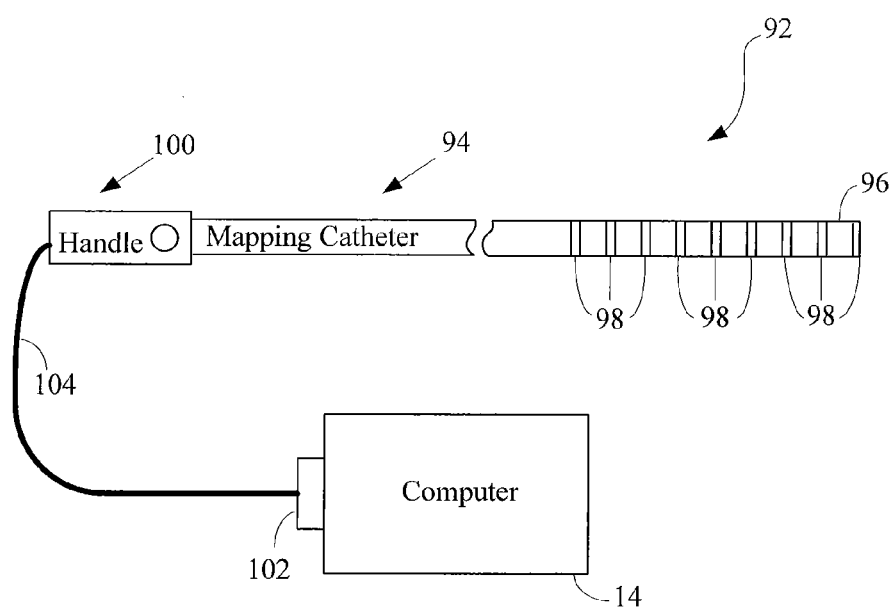
FIG. 5 is a simplified block diagram of a mapping system according to an embodiment of the present invention.

Referring additionally to FIG. 5, in other embodiments, the EP mapping procedure is performed using a mapping system 92 that includes one or more mapping catheter(s) 94 instead of the ablation catheter 12. In these embodiments, the ablation catheter still is used to ablate heart tissue 22, and can be used to perform mapping, however, on a much more limited basis. The distal end 96 of the mapping catheter includes a plurality of electrodes 98 (in some cases greater than 60 electrodes), and thus, can be used to sense in a simultaneous manner electrical signals output from the heart 24 at more than one location. The term "plurality," as used throughout this document, can mean two or more. Similar to the ablation catheter, the mapping catheter includes a steering mechanism 100, which is coupled to an interface connector 102 via an interface cable 104. The interface connector is configured to be coupled with the computer 14.

As was the case with the ablation catheter 12, the mapping catheter 94 is inserted into the heart 24 via the patient's venous system 66. When mapping the left atrium 86, the mapping catheter can be inserted into the left atrium via a hole 88 that is created in the septum 90 by the medical practitioner 32. During ablation procedures, the mapping catheter typically remains inserted in the heart at the same time that the ablation catheter is inserted in the heart. In this manner, the heart can be remapped immediately after the ablation procedure is completed without having to remove the ablation catheter and reinsert the mapping catheter.

Figure 6:
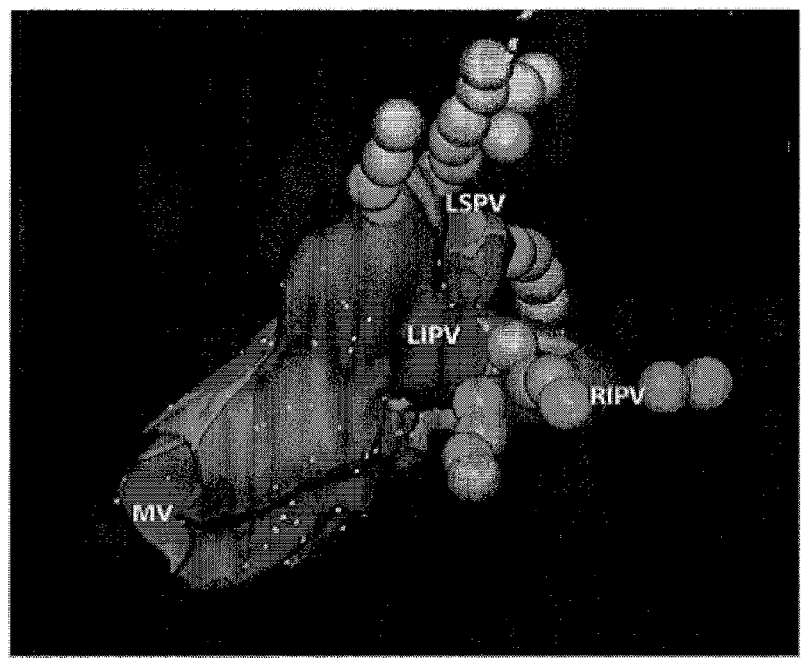
FIG. 6 is a computer-generated image of a three-dimensional map of a chamber of the patient's heart.

When a mapping catheter 94 is used, the signals that are sensed by the mapping catheter's electrodes 98 are communicated to the computer 14, where the signals are analyzed and processed for display on the user output device 62 and viewing by the medical practitioner 32. Referring again to the right-hand side of FIG. 3, in one embodiment where a mapping catheter is used, the signals that are sensed by the mapping catheter's electrodes are displayed as discrete waveforms 78, e.g., time-domain waveforms. Referring additionally to FIG. 6, in another embodiment where a mapping catheter is used, the signals sensed by the mapping catheter's electrodes are displayed in the form of a three-dimensional map 106 of a chamber 72 of the patient's heart 24, which integrates signals sensed by more than one of the mapping catheter's electrodes into the map. FIG. 6 shows the left atrium 86 including the mitral valve ("MV"), the left superior pulmonary vein ("LSPV"), the left inferior pulmonary vein ("LIPV"), and the right inferior pulmonary vein ("RIPV"). The three-dimensional map can be displayed in black and white, or in a color format.

After the mapping procedure is complete, the medical practitioner 32 selects a region of the heart tissue 22 to receive ablation energy based on an analysis of the waveforms 78. As previously discussed, the medical practitioner can determine the location of an AF driver by determining where the sensed ECG and intracardiac signals, after stimulation by the ablation catheter's electrode 26, match the ECG and intracardiac signals that result during an AF event. Next, the medical practitioner co-locates the distal end 20 of the ablation catheter 12 with the selected region.

The location of the ablation catheter's distal end 20 can be confirmed using a variety of techniques, including, for example, x-ray techniques, ultrasonic techniques, and magnetic techniques, which are know to those ordinary skill in the art. Example x-ray techniques utilize an x-ray device (not shown), e.g., a fluoroscope, to visualize the location of the ablation catheter 12 relative to the patient's cardiac system 108 after the patient 40 is injected with a contrast dye. Example ultrasonic techniques utilize an ultrasonic system (not shown) to visualize the ablation catheter, and heart 24, and other organs of the patient's body. Example magnetic techniques utilize a stereotaxic system (not shown) that includes two coils within a table upon which the patient rests. The magnetic fields sensed by the coils are used to triangulate the location of the ablation catheter in the patient's body. Finally, the medical practitioner 32 prompts the controller 16, in some embodiments via the computer 14, to deliver ablation energy to the ablation catheter, which destroys the tissue 22 that is in contact with the distal end of the ablation catheter.

In embodiments of the invention, the intracardiac signals that are sensed by the ablation catheter's electrode(s) 26 and 28 or the mapping catheter's electrodes 98 are communicated to the computer 14 and stored in a memory, i.e., a computer-readable medium 64, that is included in the computer or that is coupled to the computer. Next, the computer performs an analysis on the signals. In particular the computer calculates the mean and standard deviation of the cardiac cycle length, i.e., the length of time associated with a full heartbeat or cycle, for one or more of the intracardiac signals.

Figure 7:
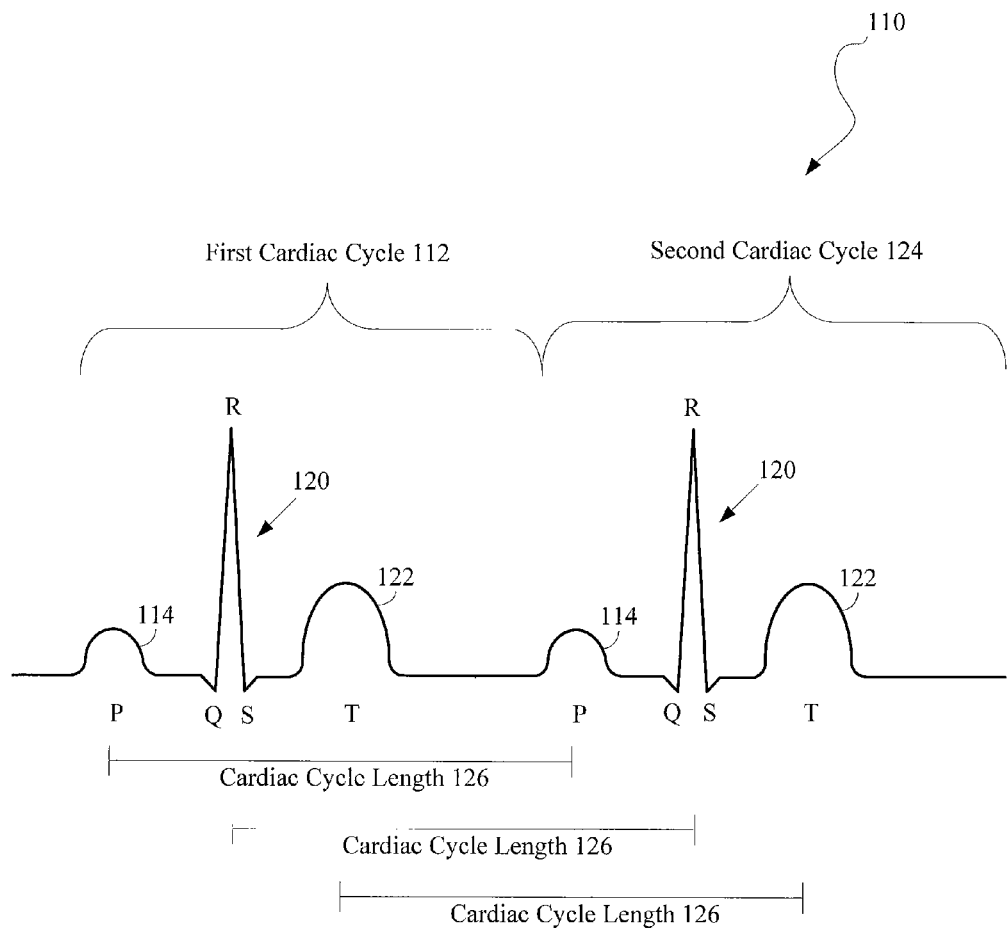
FIG. 7 is an illustration of an example ECG, which includes two cardiac cycles.

Referring additionally to the illustration of an example ECG waveform 110 in FIG. 7, in general, a cardiac cycle 112 begins with the heart's sinoatrial ("SA") node (not shown) generating a depolarization wave in the atria 82 and 86. The depolarization wave propagates throughout the atria resulting in a P wave 114. As a result of the P wave, the atria contract pushing blood into the ventricles 116 and 118. Next, the heart's atrioventricular ("AV") node (not shown) and the bundle of His (not shown) provide a propagation path for depolarization energy from the atria to the ventricles. This results in a depolarization wave propagating across the ventricles, and the ventricles contract, as exemplified in the QRS complex 120 in the ECG. Later, the ventricles repolarize resulting in a T wave 122. The next cardiac cycle 124 starts with another P wave. Thus, the cardiac cycle length 126 can be quantified as the time measured between sequential P waves, sequential QRS complexes, sequential T waves, or any other sequential and repetitive characteristic of a cardiac signal.

In embodiments of the invention, the computer's software is used to determine the cardiac cycle length 126 for each cardiac cycle 112 that is included in an intracardiac signal by performing a peak detection function on the signal. The peak detection function can be performed using a maximum signal amplitude detection scheme or a maximum change in signal amplitude detection scheme, as are known to individuals having ordinary skill in the art. Next, the software is used to sum up all of the cardiac cycle length values together. The computer's software also is used to determine the number of cardiac cycles that are included in the intracardiac signal by counting the number of cardiac cycles that occurred during the time the intracardiac signal was detected. Next, the computer's software is used to calculate the mean cardiac cycle length for the intracardiac signal by dividing the sum of the cardiac cycle length values by the number of cardiac cycles that occurred during the time of detection. During this analysis, the computer's software calculates the cardiac cycle length based on an intracardiac signal sensed at a specific location in the heart 24 for a specific period of time, e.g., upwards of approximately four seconds.

In addition to determining a mean cardiac cycle length for one or more of the intracardiac signals, the computer's software performs a cardiac cycle length variability analysis as part of the mapping process. In particular, the computer's software is used to calculate a standard deviation of the measured cardiac cycle lengths 126 based on the measured cardiac cycle lengths and the number of cycles that occurred during the length of time that the intracardiac signal was sensed. This standard deviation of cycle length value serves as an index of cardiac cycle length variability.

Cardiac cycle length variability analysis is important because it identifies the occurrence of a consistent cardiac cycle length 126. During procedures that are used to locate a driver, e.g., an AF driver, the driver can be located by finding the location in the heart 24 that has the lowest cardiac cycle length variability, i.e., the smallest standard deviation of cycle length value.

Figure 8:
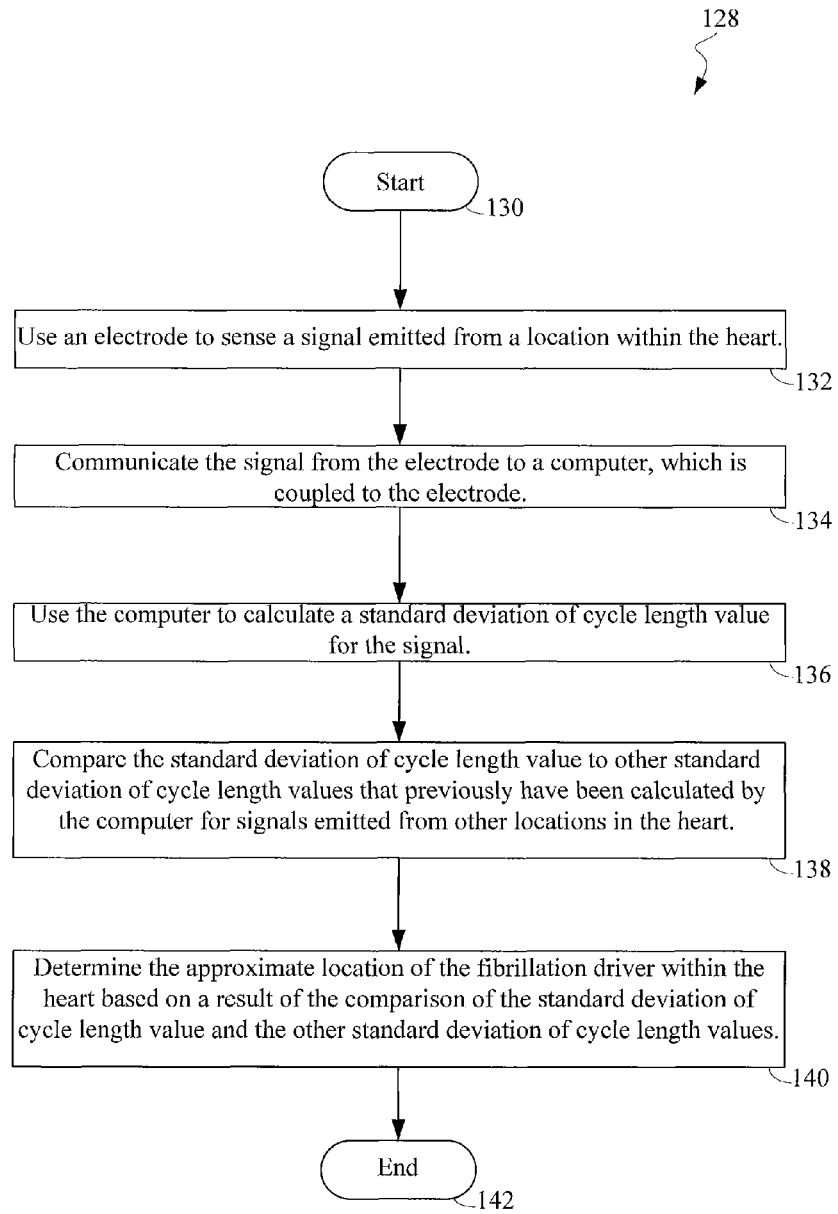
FIG. 8 is a flow diagram of an exemplary algorithm according to the present invention.

Thus, in general, the cardiac cycle length variability analysis can be shown in the exemplary algorithm 128 illustrated in FIG. 8. After the algorithm starts at step 130, an electrode 26 or 98 is used to sense a signal that is emitted from a location within the heart 24 at step 132. At step 134, the signal is communicated from the electrode to a computer 14, which is coupled to the electrode. At step 136, the computer is used to calculate a standard deviation of cycle length value for the signal. Next, at step 138, the standard deviation of cycle length value is compared to other standard deviation of cycle length values that previously have been calculated by the computer for signals emitted from other locations within the heart. At step 140, an approximate location of the fibrillation driver is determined based on the comparison of the standard deviation of cycle length value and the other standard deviation of cycle length values. Finally, the algorithm ends at step 142.

Figure 3:
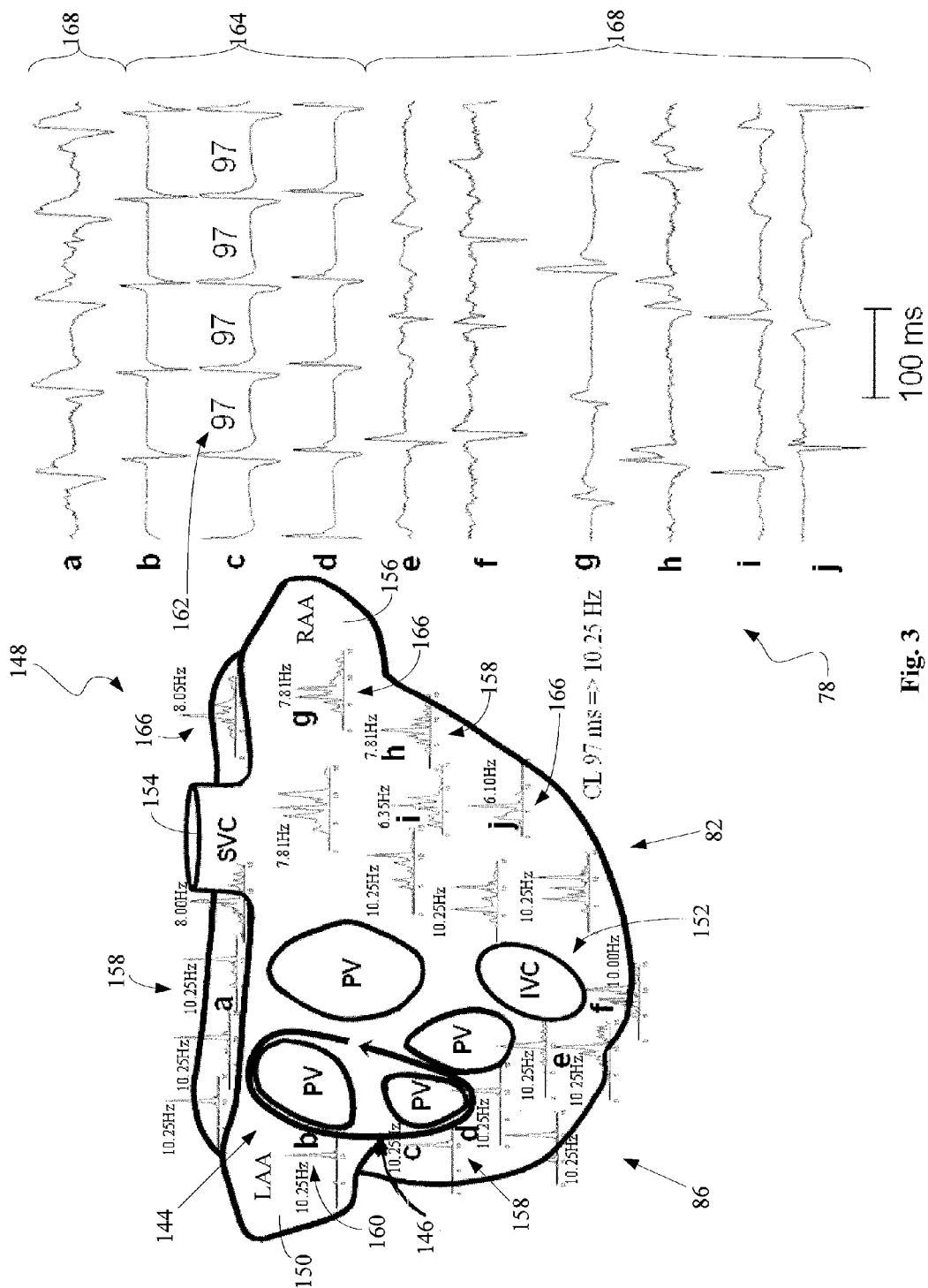
FIG. 3 is an illustration of the left atrium and the right atrium of the patient's heart including frequency waveforms and time-domain waveforms.

Example measurements of cardiac cycle length 126 are shown in the atrial electrograms 78 shown in the right-hand side of FIG. 3. The right-hand side of FIG. 3 includes atrial electrograms for an AV event caused by a stable reentrant circuit (an "AF driver") that is located near the pulmonary veins ("PVs") 144 (see the left-hand side of FIG. 3). The reentrant circuit is represented in FIG. 3 by the curved arrow 146. The left-hand side of FIG. 3 is a graphical depiction 148 of the left atrium 86 and the right atrium 82 of a patient's heart 24 (the ventricles 116 and 118 are not shown in FIG. 3) with the following regions of the heart specifically identified: the left atrial appendage ("LAA") 150, the PVs in cross-section, the inferior vena cava ("IVC") 152 in cross-section, the superior vena cava ("SVC") 154 in cross-section, and the right atrial appendage ("RAA") 156. The left-hand side of FIG. 3 also includes frequency spectrum waveforms 158 that resulted from Fast Fourier Transform ("FFT") analyses of time-domain, intracardiac signals sensed by the ablation catheter 12 or mapping catheter 94 at various locations in the heart. More specifically, the position of each of the frequency spectrum measurement diagrams is located approximately where its respective time-domain, intracardiac signal was sensed.

The right-hand side of FIG. 3 includes the various time-domain atrial electrograms (see a through j) 78 that correspond to the frequency spectrum waveforms 158 shown in the left-hand side of FIG. 3. The approximate location where each of the time-domain measurements were taken in the left atrium 86 and the right atrium 82 are identified in the left-hand side of FIG. 3, with the corresponding letters a through j. The computer 14 and its software are configured to perform the FFT analyses on the time-domain intracardiac signals. While frequency spectrum waveforms are included in FIG. 3, embodiments of the invention need not perform an FFT analysis in addition to the cardiac cycle length variability analysis, as part of the process for determining the location the driver.

As shown in the frequency spectrum waveforms 158, a well-defined dominant peak frequency 160 of approximately 10.25 Hz occurred near the left atrial appendage 150. This corresponds to a uniform cardiac cycle length 126 of approximately 97 milliseconds 162, as shown in time-domain electrograms b, c, and d 164. The other frequency spectrum waveforms, which correspond to time-domain measurements taken at locations in the heart 24 other than locations b, c, and d, include additional and different peaks 166. In particular, multiple peaks having frequencies ranging from approximately 6.34 Hz to approximately 10.25 Hz are included in the frequency spectrum waveforms for locations in the right atrium 82. These additional peaks are associated with fibrillatory conduction that is caused by wavefronts from the reentrant circuit 146 in the left atrium 86. These additional peaks in the frequency spectrum waveforms correspond to less-uniform, time-domain measurements, which are visually noticeable in the time-domain electrograms for locations a and e-j 168. Because the time-domain waveforms for locations a and e-j are less uniform than the time-domain waveforms for locations b, c, and d, it is expected that the standard deviation of the cardiac cycle length would be greater for locations a and e-j, than for locations b, c, and d, as shown in the following table.

| Location | Mean Cycle Length Value (milliseconds) | Standard Deviation of Cycle Length Value (milliseconds) |
|---|---|---|
| a | 98.9 | 1.4 |
| b | 98.6 | 1.5 |
| c | 97.3 | 0.5 |
| d | 98.4 | 1.0 |
| e | 127.1 | 18.3 |
| f | 112.6 | 30.6 |
| g | 124.1 | 14.6 |
| h | 155.7 | 17.5 |
| i | 117.6 | 29.3 |
| j | 129.8 | 23.1 |

FFT analysis has increasing been used to assist the study and characterization of atrial arrhythmias. In particular, FFT analysis has been used to convert time-domain data into a sum of sinusoidal functions that are multiplied by coefficients. Thus, FFT analysis can be thought of as a method for decomposing a time-domain signal into its component frequencies and related amplitudes, which are quantified by the coefficients. FFT analysis rapidly and accurately can identify regular and irregular patterns of atrial activation during different types of atrial tachyarrhythmias. This rapid identification of the type of activation can be used by the medical practitioner 32 when determining the location of a driver, be it a focus or a reentrant circuit, and thus, potentially assist in clinical decisions and approaches toward therapeutic interventions such as catheter ablation and the MAZE surgical procedure.

One limitation of FFT analysis is its lack of sensitivity due to the frequency resolution of the FFT analysis. For example, the FFT analysis will include a single dominant peak 160 for regions of the heart 24 that have regular and periodic activation, and the FFT analysis will include multiple peaks 166 for regions of the heart that have irregular activation. This distinction assists the medical practitioner 32 during efforts to locate general regions of the heart that have regular and periodic activation; however, it does not accurately pinpoint the location of a driver. In particular, due to this frequency resolution limitation, intracardiac signals having varying cardiac cycle length 126 with standard deviations within the frequency resolution of the FFT analysis will still have a single dominant frequency peak. This deficiency in the FFT analysis is overcome by using cardiac cycle length variability analysis according to embodiments of the present invention.

Another limitation that is associated with FFT analysis is its inability to demonstrate activation sequence. FFT analysis can be used to determine global activation patterns; however, FFT analysis can not be used to determine a detailed sequence of activation because the analysis is done in the frequency domain, and not the time domain.

However, in embodiments of the present invention, a medical practitioner 32 may perform FFT analysis before performing the cardiac cycle length variability analysis. In particular, the medical practitioner may perform an FFT analysis of the entire patient's heart 24 or a region of the heart, e.g., a chamber 72 of the heart, and then, perform the cardiac cycle length variability analysis on only a small region of the heart that includes a location having an FFT with a single frequency peak and/or a high frequency value. Thus, by performing the FFT analysis first, and then performing a high-density cardiac cycle length variability analysis of a limited region of the patient's heart, the medical practitioner can obtain a more efficient and more accurate approximation of the location of the driver. Accordingly, the location of a driver in a patient's heart can be approximated using FFT analysis and/or cardiac cycle length variability analysis. Typically, greater accuracy in determining the driver's location is obtained using the cardiac cycle length variability analysis in combination with the FFT analysis.

Figure 9:
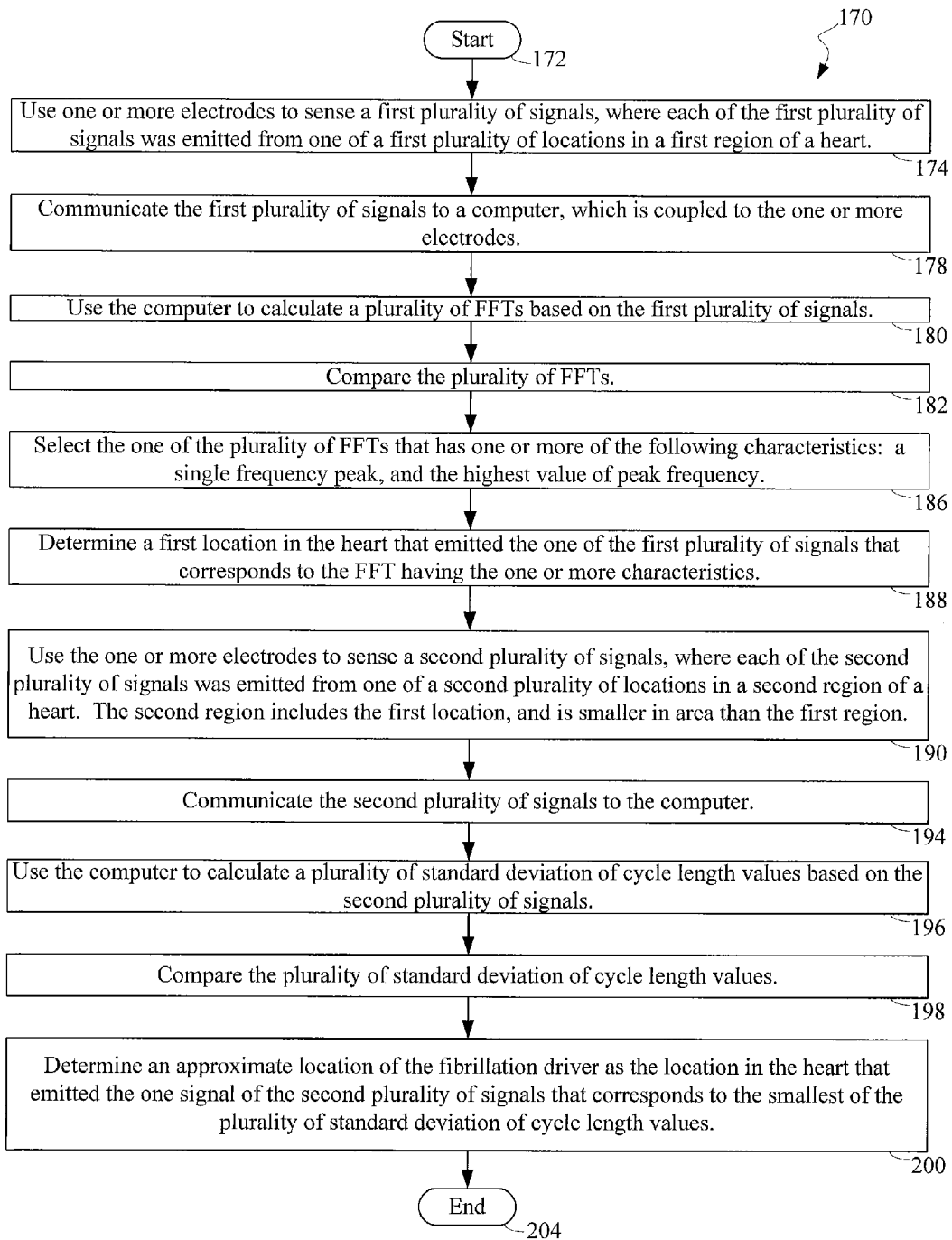
FIG. 9 is a flow diagram of another exemplary algorithm according to the present invention.
Figure 10:
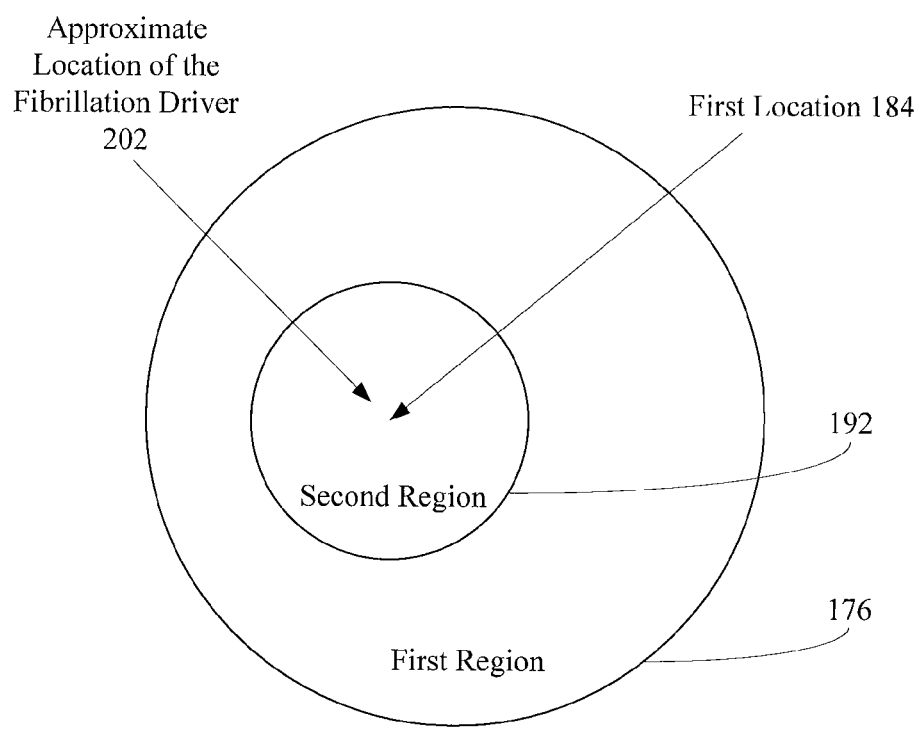
FIG. 10 is a simplified diagram of regions in the patient's heart.

FIG. 9 is an exemplary algorithm 170 according to the present invention that includes an FFT analysis followed by a cardiac cycle length variability analysis. After the algorithm starts at step 172, one or more electrodes 26, 28, and 98, which are coupled to a computer 14, are used to sense a first plurality of signals at step 174. Each of the first plurality of signals were emitted from one of a first plurality of locations in a first region 176 (see FIG. 10) of the heart 24. While the first region of the heart is represented as a circle in FIG. 10, the first region can be any shape. Next, at step 178, the first plurality of signals is communicated to the computer, which is used to calculate a plurality of FFTs based on the first plurality of signals at step 180. At step 182, the plurality of FFTs is compared, and a first location 184 in the heart is selected that has one or more of the following characteristics: a single frequency peak 160 and the highest value of peak frequency at steps 186 and 188.

Next, at step 190, the one or more electrodes 26, 28, and 98 are used to sense a second plurality of signals. Each of the second plurality of signals was emitted from one of a second plurality of location in a second region 192 of the heart 24. The second region of the heart includes the first location 184 and is smaller in area than the first region 176. While the second region of the heart is represented as a circle in FIG. 10, the second region can be any shape. At step 194, the second plurality of signals are communicated to the computer 14, which is used to calculate a plurality of standard deviation of cycle length values based on the second plurality of signals at step 196.

At step 198, the plurality of standard deviation of cycle length values are compared. Next, at step 200, an approximate location of the fibrillation driver 202 in the heart 24 is determined. The approximate location is the location in the heart that emitted the one signal of the second plurality of signals that corresponds to the smallest of the plurality of standard deviation of cycle length values. The algorithm ends at step 204.

For the AF event shown in FIG. 3, the location that has the minimum amount of cardiac cycle length variability, and thus, the minimum value of standard deviation of cycle length, is the location of the reentrant circuit 146. Accordingly, once the system 10 and 92 is used to determine the location in the heart 24 that has the minimum standard deviation of cycle length, the medical practitioner 32 will use the ablation catheter 12 to apply ablation energy to that location in an effort to eliminate the reoccurrence of the AF event.

Figure 11:
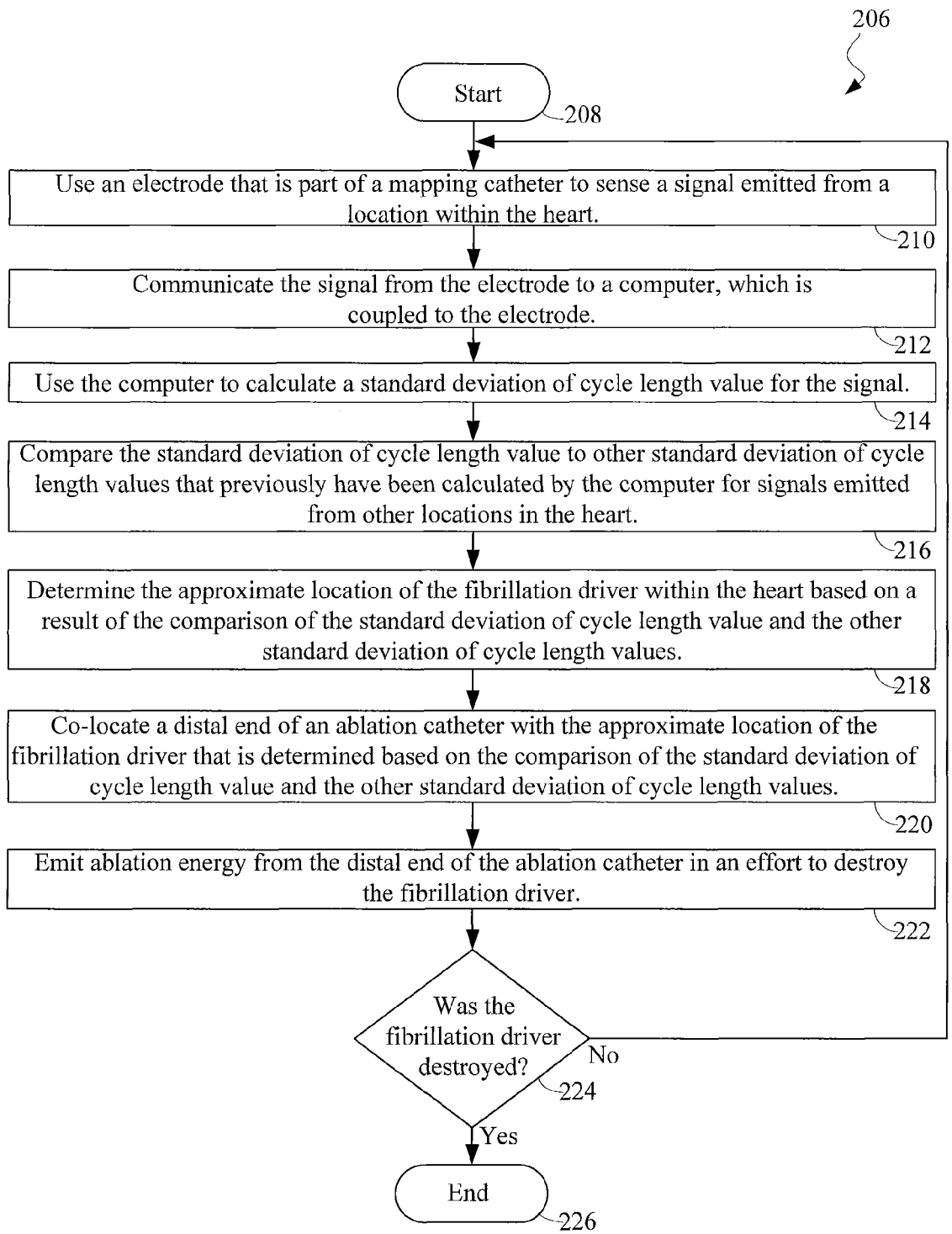
FIG. 11 is a flow diagram of another exemplary algorithm according to the present invention, which can be implemented using the ablation system of FIG. 1.

Typically, after the ablation energy is applied to a location in the heart 24, the region around that location is retested using the ablation catheter 12 and/or a mapping catheter 94. The cardiac cycle length variability analysis will be repeated for the retested locations, and ablation energy may be reapplied to the original location or another location depending upon the results of the analysis. Typically, this process of mapping, performing the cardiac cycle length variability analysis, and ablating will be repeated until the medical practitioner 32 is satisfied that the driver has been eliminated, as shown in the exemplary algorithm 206 illustrated in FIG. 11.

In the exemplary algorithm 206, after the algorithm starts at step 208, an electrode 98 that is part of a mapping catheter 94 is used to sense a signal that is emitted from a location within the heart 24 at step 210. At step 212, the signal is communicated from the electrode to a computer 14, which is coupled to the electrode. At step 214, the computer is used to calculate a standard deviation of cycle length value for the signal. Next, at step 216, the standard deviation of cycle length value is compared to other standard deviation of cycle length values that previously have been calculated by the computer for signals emitted from other locations within the heart.

At step 218, the approximate location of the fibrillation driver is determined based on the comparison of the standard deviation of cycle length values. Next, at step 220, the user 32 co-locates the distal end 20 of the ablation catheter 12 with the approximate location of the fibrillation driver that is determined based on the comparison of the standard deviation of cycle length values. At step 222, ablation energy is emitted from the distal end of the ablation catheter in an effort to destroy the fibrillation driver. Next, at step 224, it is determined if the fibrillation driver was destroyed. If the fibrillation driver was destroyed, then the algorithm ends at step 226. If the fibrillation driver was not destroyed, then the steps of sensing the signal with the electrode 98, calculating the standard deviation of cycle length value for the signal, comparing the standard deviation of cycle length values, determining the approximate location of the fibrillation driver, co-locating the distal end of the ablation catheter with the approximate location, and emitting the ablation energy are repeated until the fibrillation driver is destroyed.

In embodiments that include the use of a mapping catheter 94 and the display of the resulting data superimposed on a three-dimensional map 106 of a chamber of the heart 24, various data, e.g., the mean cardiac cycle length and/or the standard deviation of cycle length, can overlay the three-dimensional map. In this manner the medical practitioner 32 can compare the data simultaneously. Also, in other embodiments, the data is color-coded depending upon the data type, e.g., cycle length data versus standard deviation of cycle length data, or depending upon the data values, e.g., standard deviation of cycle length values within a specific range are one color, while standard deviation of cycle length values that are outside the specific range are another color. In addition to overlapping cycle length data and standard deviation of cycle length data onto the three-dimensional map of a chamber of the heart, FFT spectrum data 158 can also be overlapped onto the map. In this way, the medical practitioner can view the FFT spectrum data along with the cycle length data and/or the standard deviation of cycle length data.

In additional embodiments, the location on the three-dimensional map 106 having the minimal value of standard deviation of cycle length is highlighted, e.g., color-coded (in this document the meaning of the term "highlight" includes to make more visible or prominent, e.g., by adding an area of lightness or an annotation. The highlighted map can be a map of the heart 24 with or without one or more of the following data overlapping the map: the FFT spectrum 158, the mean cycle length data, and the standard deviation of cycle length data. In embodiments where a three-dimensional map of a chamber of the heart is not presented to the medical practitioner 32, and only electrograms 78 are displayed (see the right-hand side of FIG. 3), the electrogram that has the minimal standard deviation can be highlighted for viewing by the medical practitioner. Because the map or electrogram is highlighted, it reduces the amount of time spent by the medical practitioner identifying the location associated with the smallest standard deviation of cycle length value.

Figure 12:
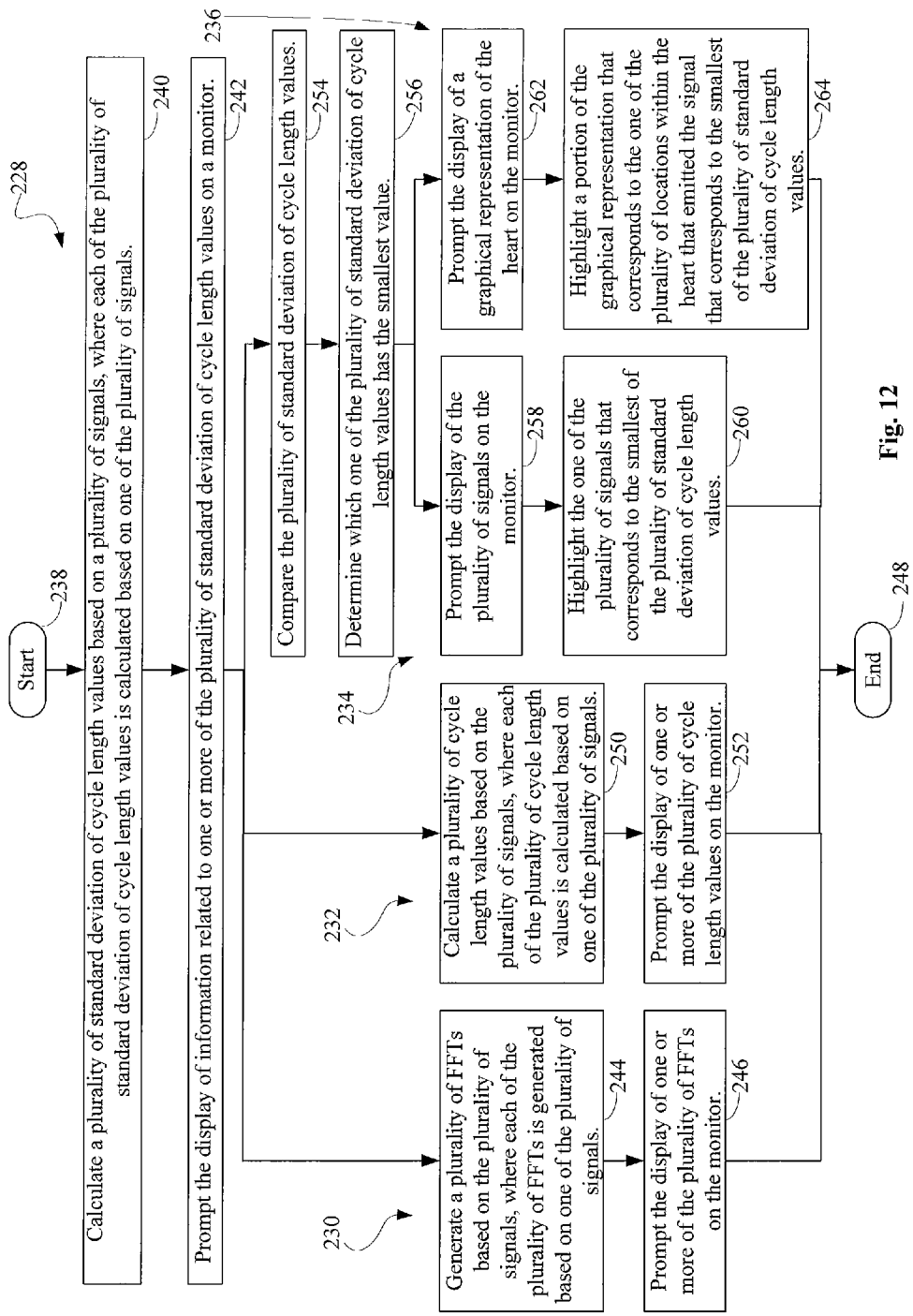
FIG. 12 is a flow diagram of another exemplary algorithm according to the present invention, which can be implemented by the ablation system of FIG. 11 and/or the mapping system of FIG. 5.

FIG. 12 is an exemplary algorithm 228 that details steps taken by the computer's software, which can be stored in a computer-readable medium 64. In particular, the steps of the exemplary algorithm are initiated by program instructions included in the computer's software. The exemplary algorithm includes four different braches 230-236, which represent four different methods of displaying data. Before reaching the four branches, the algorithms starts at step 238, followed by step 240, where a plurality of standard deviation of cycle length values are calculated based on a plurality of signals. Each of the plurality of standard deviation of cycle length values is calculated based on one of the plurality of signals. Next, at step 242, the software prompts the display of information that is related to one or more of the plurality of standard deviation of cycle length values on the computer's monitor 62.

In the first branch 230 of the algorithm 228, at step 244, the software generates a plurality of FFTs based on the plurality of signals. Each of the plurality of FFTs is generated based on one of the plurality of signals. Next, at step 246, the software prompts the display of one or more of the plurality of FFTs on the monitor 62. The first branch of the algorithm ends at step 248.

In the second branch 232 of the algorithm 228, at step 250, the software calculates a plurality of mean cycle length values based on the plurality of signals. Each of the plurality of mean cycle length values is calculated based on one of the plurality of signals. Next, at step 252, the software prompts the display of one or more of the plurality of mean cycle length values on the monitor 62. The second branch of the algorithm ends at step 248.

In the third and fourth branches 234 and 236, respectively, of the algorithm 228, at step 254, the software compares the plurality of standard deviation of cycle length vales. Next at step 256, the software determines which one of the plurality of standard deviation of cycle length values has the smallest value.

Additionally, in the third branch 234 of the algorithm 228, at step 258, the software prompts the display of the plurality of signals on the monitor 62. Next, at step 260, the software highlights the one signal of the plurality of signals that corresponds to the smallest of the plurality of standard deviation of cycle length values. The third branch of the algorithm ends at step 248.

Furthermore, in the fourth branch 236 of the algorithm 228, at step 262, the software prompts the display of a graphical representation of the heart 24 on the monitor 62. Next, at step 264, the software highlights a portion of the graphical representation of the heart that corresponds to the location within the heart that emitted the signal that corresponds to the smallest of the plurality of standard deviation of cycle length values. The fourth branch of the algorithm ends at step 248.

Advantageously, the cardiac cycle length variability analysis according to embodiments of the invention can be used by a medical practitioner 32 to quickly and accurately determine the location of a driver during an ablation procedure. The cardiac cycle length variability analysis can be performed on the intracardiac signals that would be recorded during a conventional EP mapping process. Thus, the cardiac cycle length variability analysis need not require any additional intracardiac signal measurements. Also, embodiments of the invention minimize the length of time spent by the medical practitioner during the EP mapping process. In addition, the number of times that ablation energy is delivered to the heart tissue 22 is minimized because the location of the driver is determined in an accurate manner.

Figure 13:
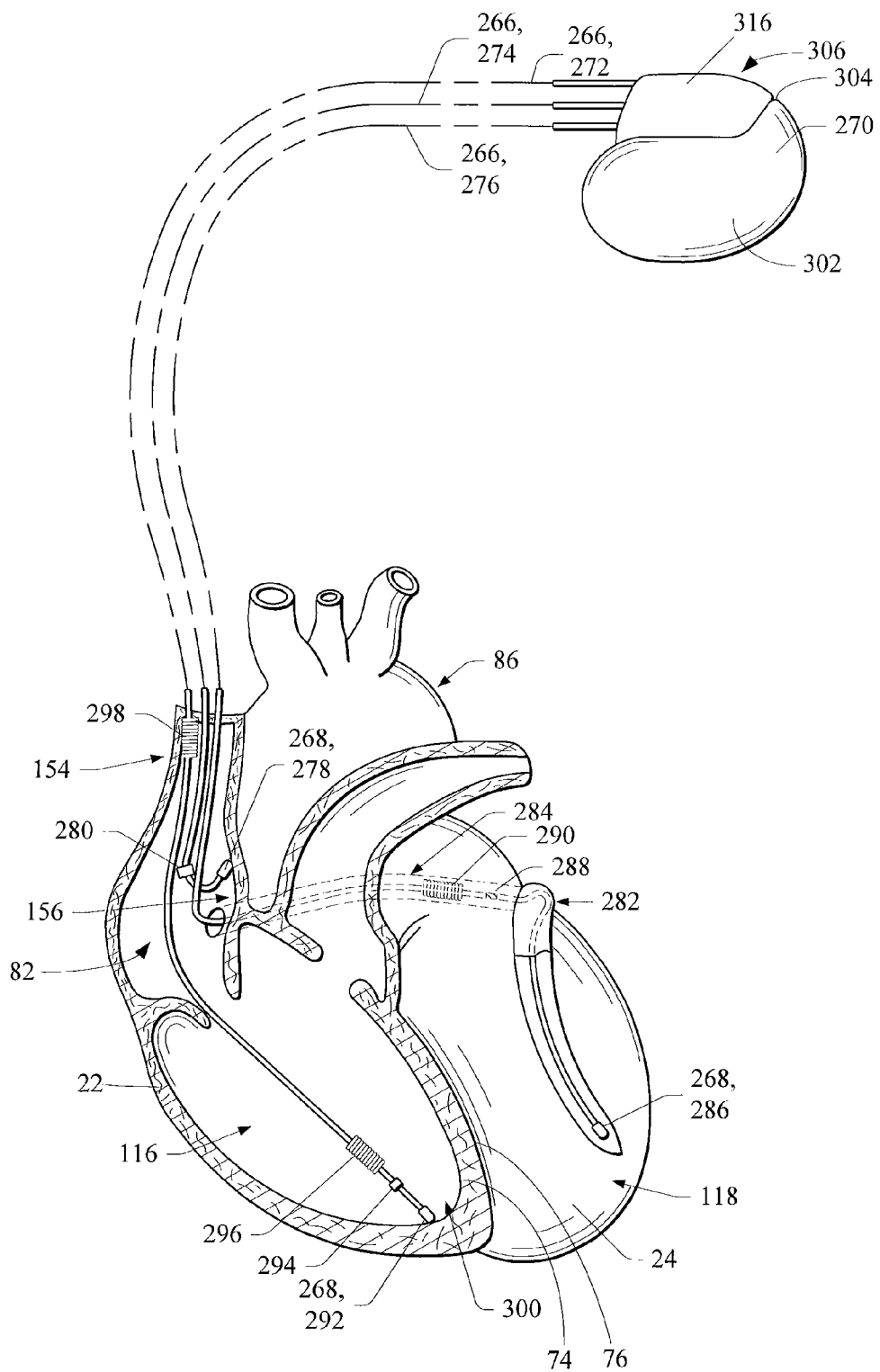
FIG. 13 is a simplified diagram that illustrates an IMD, which is electrically coupled to three IMD leads that are positioned within the patient's heart.

Referring additionally to FIG. 13, in addition to using embodiments of the invention during ablation procedures, embodiments of the invention also can be used during the installation of an IMD lead 266 in a patient's heart 24. In particular, embodiments can be used during the installation of an IMD lead so that a lead electrode 268 that is included in the lead is co-located with, i.e., positioned adjacent to, a driver. As was previously discussed, a lead electrode that is co-located with a driver can be used in therapeutic efforts to prevent fibrillation.

Although embodiments of the present invention can be used in conjunction with a wide variety of IMDs 270, with reference now to FIG. 13, there is shown an exemplary IMD, a heart stimulation device, in its fully installed configuration. The IMD is in electrical communication with a patient's heart 24 by way of three leads 272, 274, and 276, which are suitable for delivering multi-chamber stimulation and shock therapy. To sense atrial cardiac signals and to provide right atrial chamber stimulation therapy, the IMD is coupled to an implantable right atrial lead 274 having at least an atrial tip electrode 278, which typically is implanted in the patient's right atrial appendage 156. As shown in FIG. 13, the right atrial lead also includes a right atrial ring electrode 280.

To sense left atrial and ventricular cardiac signals and to provide left chamber pacing therapy, the IMD 270 is coupled to a coronary sinus lead 276, which is designed for placement in the coronary sinus region 282 via the coronary sinus 284 for positioning a distal electrode 286 adjacent to the left ventricle 118 and/or additional electrode(s) 288 and 290 adjacent to the left atrium 86. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein, or any other cardiac vein accessible by the coronary sinus. Accordingly, an exemplary coronary sinus lead is designed to receive atrial and ventricular cardiac signals and to deliver left ventricular pacing therapy using at least a left ventricular tip electrode 286, left atrial pacing therapy using at least a left atrial ring electrode 288, and shocking therapy using at least a left atrial coil electrode 290.

In FIG. 13, the IMD 270 also is shown in electrical communication with the patient's heart 24 by way of an implantable right ventricular lead 272 having, in this implementation, a right ventricular tip electrode 292, a right ventricular ring electrode 294, a right ventricular ("RV") coil electrode 296, and a superior vena cava ("SVC") coil electrode 298. Typically, the right ventricular lead is transvenously inserted into the heart so as to place the right ventricular tip electrode in the right ventricular apex 300 so that the RV coil electrode will be positioned in the right ventricle 116 and the SVC coil electrode will be positioned in the superior vena cava 154. Accordingly, the right ventricular lead is capable of sensing or receiving cardiac signals, and delivering stimulation in the form of pacing and shock therapy to the right ventricle.

The IMD 270 includes a housing 302, which often is referred to as the "can", "case", or "case electrode", and can be selected programmably to act as the return electrode for all "unipolar" modes of operation for the IMD. Furthermore, the housing can be used as a return electrode alone, or in combination with, one or more of the coil electrodes 290, 296, and 298 for shocking purposes. The housing further includes a connector assembly 304 that is configured to interface with the proximal end 306 of the leads 266.

The IMD 270 can be configured to treat both fast and slow arrhythmias with stimulation therapy, including cardioversion, defibrillation, and pacing stimulation. While a particular multi-chamber device is shown in FIG. 13, it is to be appreciated and understood that this is done for illustration purposes only. Thus, the techniques and methods described below can be implemented in connection with any suitably configured or configurable heart stimulation device.

Figure 14:
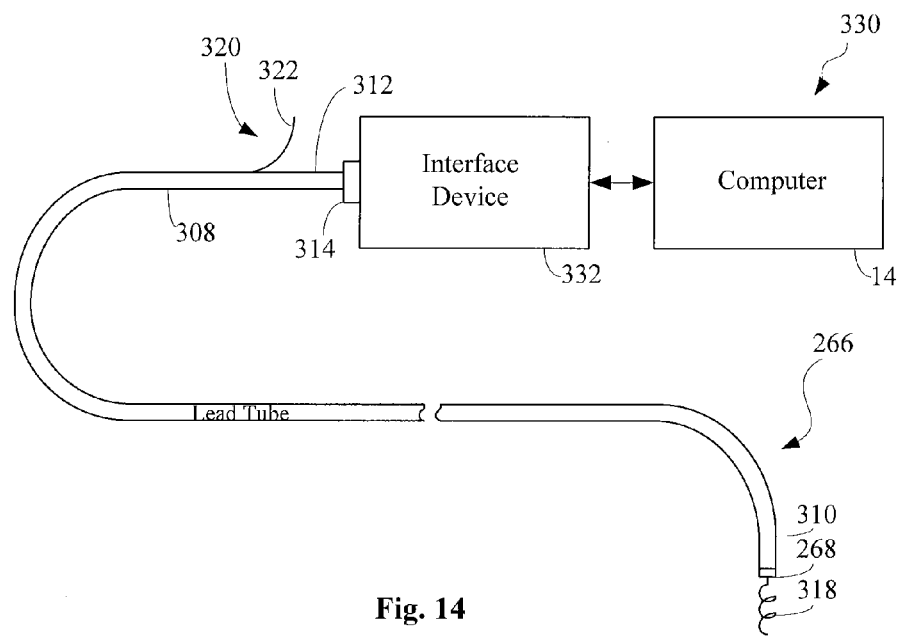
FIG. 14 is a simplified block diagram of an IMD lead installation system according to an embodiment of the present invention.

Referring additionally to FIG. 14, typically, each IMD lead 266 includes a flexible tube 308 made of, for example, silicone, polyurethane, and/or other biocompatible, implantable, dielectric materials having insulating capabilities. The flexible tube can have a diameter ranging from approximately 4 French to approximately 9 French and length ranging from approximately 50 centimeters to approximately 90 centimeters. The IMD lead includes a distal end 310, which is configured to be inserted into the patient's heart 24, and a proximal end 312, which includes a lead connector 314, which is configured to be coupled to the IMD 270 via a connector assembly 316. The flexible tube can be straight, or formed into a preferred shape for implantation.

The distal end 310 of the IMD lead 266 includes a lead electrode 268 that is coupled electrically to the lead connector 314 via a conductor (not shown), e.g., a helical wire, which is located within the flexible tube 308 and that runs the length of the lead. The lead electrode is configured to be used by the IMD 270 to sense intracardiac electrical signals generated by the heart 24 and to deliver electrical stimulation from the IMD to the heart. Typically, the distal end of the IMD lead also includes a fixation device 318, e.g., a tine or a helical screw, which is configured to interface with the heart tissue 22 and may be electrically coupled to the lead electrode. The fixation device is used to secure the distal end of the IMD lead to the heart tissue in such as manner that the lead electrode is brought into secured contact with the heart tissue. The medical practitioner 32 engages the fixation device with the heart tissue after he or she has determined that the distal end of the IMD lead is co-located with heart tissue that has desired conductivity properties. In the case of a fixation device that includes a helical screw, after the medical practitioner determines that the distal end of the IMD lead is at the correct location, the medical practitioner will rotate the IMD lead, which, in turn, screws the helical screw into a secured position in the heart tissue.

As was the case in the previously discussed ablation catheter 12, the IMD lead 266 includes a steering mechanism 320 that allows a medical practitioner 32 to move the distal end 310 of the IMD lead when the IMD lead is being installed in the patient's heart 24. The lead's steering mechanism usually includes a stylet or guide wire 322, which the medical practitioner inserts into the lead through its proximal end 312. The medical practitioner maneuvers the distal end of the lead by applying force to the guide wire, and by rotating the lead.

Figure 15:
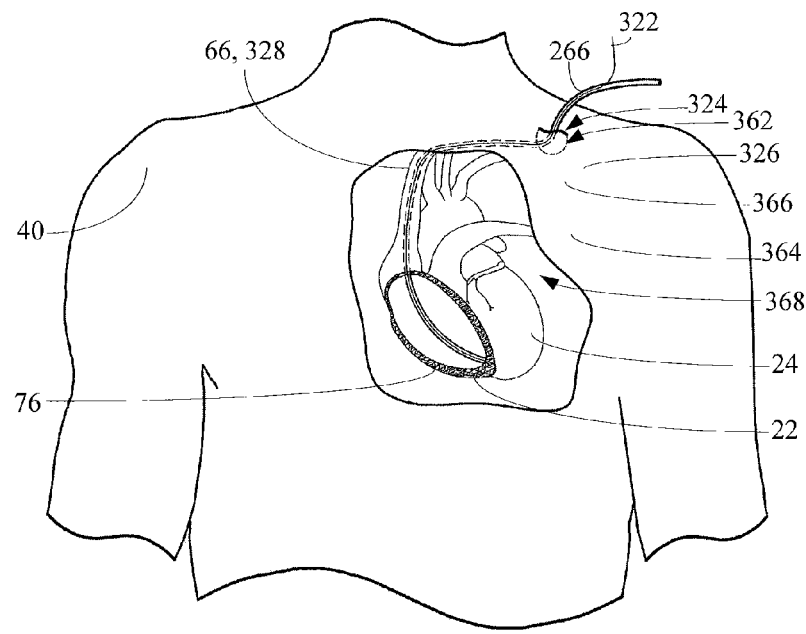
FIG. 15 is a partial cross-sectional front view of a patient's body with an IMD lead inserted into the patient's heart.

Referring to FIG. 15, during endocardial installation of the IMD leads 266, a medical practitioner 32 creates a small incision 324 in the patient's chest 326, and each of the IMD leads is inserted individually through the incision and the patient's venous system 66 into the heart 24. Typically, the IMD leads are inserted into the patient's venous system through an incision in the patient's subclavian vein 328. Once the distal end 310 of the IMD lead is located within the heart, the medical practitioner uses the steering mechanism 320 to direct the lead electrode 268 into contact with the tissue 22 of the heart. The medical practitioner can use a variety of techniques, including, for example, x-ray techniques (e.g., fluoroscopic observation), ultrasonic techniques, and/or magnetic techniques, known to individuals having ordinary skill in the art to help determine and/or confirm the position of the distal end of the lead within the patient's heart.

During the lead installation process, the medical practitioner 32 typically will map the region of the heart 24 where the IMD lead 266 is to be installed for its electrical characteristics before the IMD lead is fixed in place. The mapping can be done using the lead electrode 268 and/or a mapping catheter 94. Referring again to FIG. 14, in one embodiment where only the lead electrode is used to map the electrical characteristics of the heart, the IMD lead is coupled to a system 320 that includes an interface device 332, which is coupled to a computer 14. The interface device is configured to amplify the intracardiac signals that are sensed by the lead electrode. The amplified signals are communicated to the computer, which is configured to display the intracardiac signals and measured values that are related to the cardiac signal on a user output device 62, e.g., a monitor, and stored in the computer's memory, i.e., a computer-readable medium 64.

In embodiments where the IMD lead 266 is used during the mapping process, the intracardiac signals are sensed at a specific location in the heart 24 for upwards of approximately four seconds. In one embodiment, the resulting time-domain, intracardiac signals 78 are displayed on the monitor 62 for viewing by the medical practitioner 32. In this configuration, the intracardiac signals that are sensed using the IMD lead typically are presented to the medical practitioner as a single signal waveform for each location in the heart. Next, the computer 14, as part of the mapping process, is configured to perform an analysis of each of the intracardiac signals, including a calculation of the mean cardiac cycle length and the cardiac cycle length variability, for each location, as previously discussed.

Figure 16:
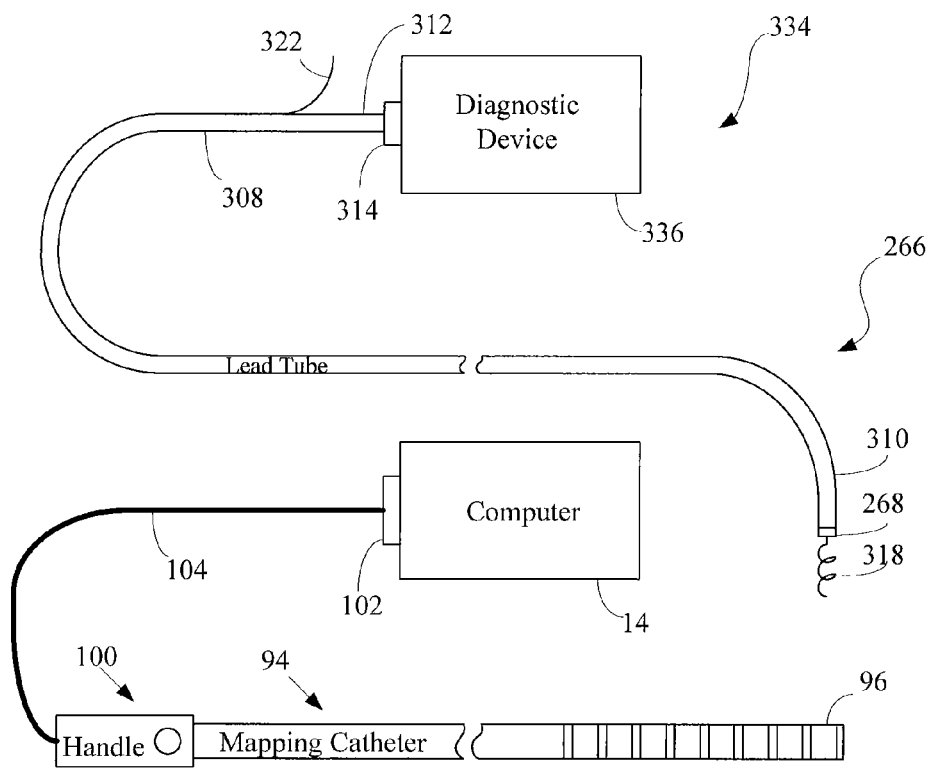
FIG. 16 is another simplified block diagram of an IMD lead installation system according to an embodiment of the present invention in combination with the mapping system of FIG. 5.

Referring additionally to FIG. 16, in other embodiments, the IMD lead 266 is not used during the mapping process, rather, a mapping catheter 94, which is coupled to a computer 14, is used to map the heart 24. In these embodiments, the IMD lead is coupled to another system 334 that includes a diagnostic device 336, rather than the interface device 332. The diagnostic device is configured to receive the electrical signals sensed by the lead electrode 268, and to measure, for example, pacing threshold, signal amplitude, and lead impedance. In these embodiments, the mapping procedure is performed using the mapping catheter in combination with the computer, as was previously described for the ablation procedure. When the mapping catheter is used, the resulting data can be displayed on the user output device 62 as waveforms 78 and 158 and/or a three-dimensional map 106 with overlays, as previously discussed. After the mapping procedure is complete, the mapping catheter is removed from the patient 40, and the IMD lead is inserted into its desired location in the heart.

During the lead installation process, the cardiac cycle length variability analysis is valuable because it assists the medical practitioner 32 with co-locating a lead electrode 268 with a driver in the heart 24. As previously discussed, the location of the driver will have associated with it the smallest cardiac cycle length variability, i.e., smallest standard deviation of cycle length value. After the mapping procedure is complete, the medical practitioner will move the distal end 310 of the IMD lead 266 so that the lead electrode contacts the location in the heart tissue 22 that has the smallest cardiac cycle length variability. This will be the location where the medical practitioner will secure the position of the lead electrode relative to the heart tissue using the fixation device 318.

Typically, before securing the IMD lead 266 in place, the medical practitioner 32 will apply an electrical pulse via the lead electrode 268 to the heart tissue 22 and monitor the response of the heart 24 to the electrical stimulus using the diagnostic device 336 or the computer 14. If the medical practitioner determines that the lead electrode is not co-located with the driver, then the medical practitioner may attempt to remap a portion of the heart, using the IMD lead and/or the mapping catheter 94 in an effort to relocate the driver, based on the value of the standard deviation of cycle length.

Figure 17:
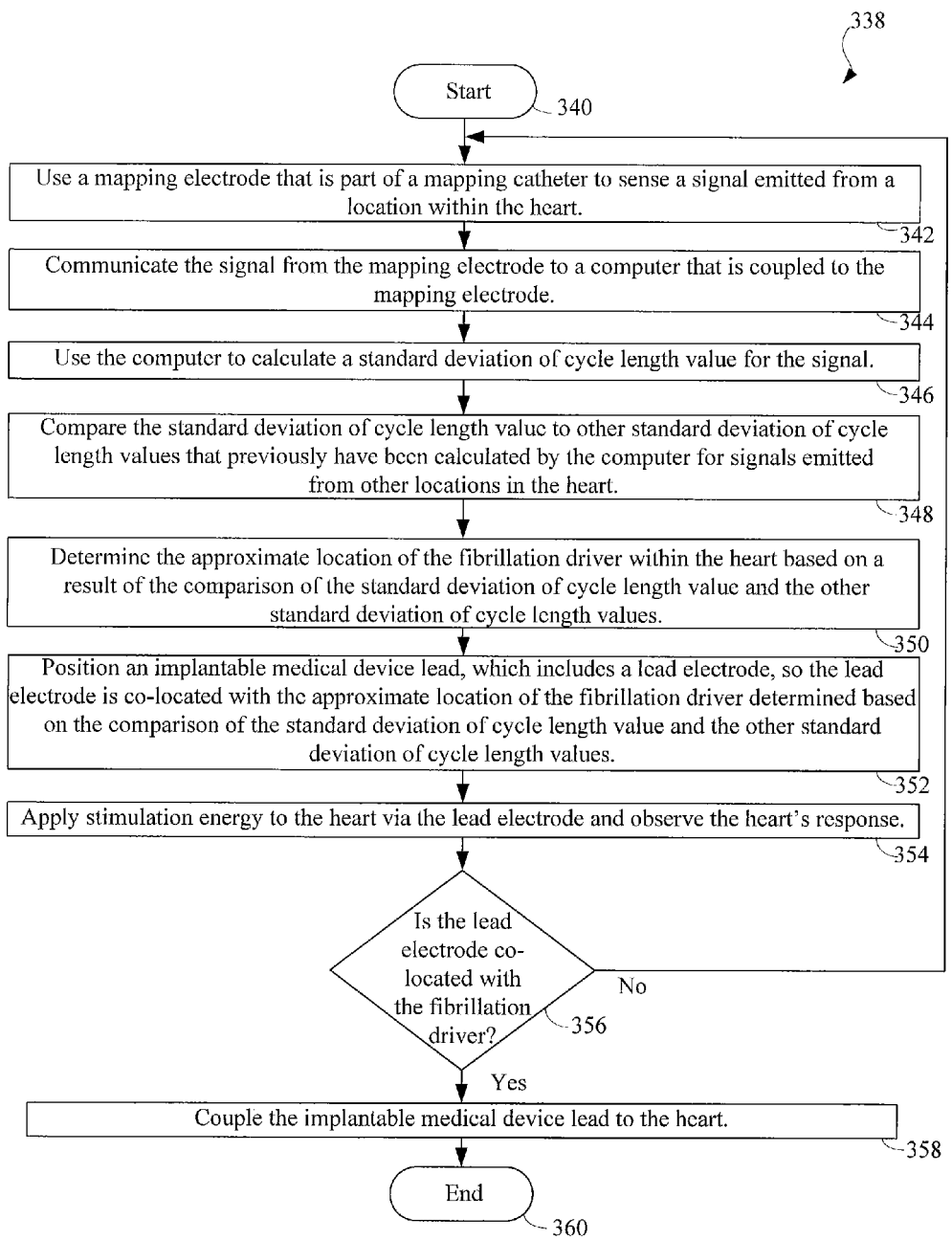
FIG. 17 is a flow diagram of another exemplary algorithm according to the present invention, which can be implemented by the IMD lead installation systems of FIGS. 11 and 13.

The procedure of mapping the heart 24, positioning the lead electrode 268 in contact with the heart tissue 22 at a suspected location of the driver, electrically stimulating the heart tissue at that location, and confirming the response of the heart 24 to the stimulation can be repeated by the medical practitioner 32 until he or she is confident that the lead electrode is in its optimal location, i.e., the lead electrode is co-located with the driver. At which point, the medical practitioner will couple the IMD lead 266 to the heart tissue using the fixation device 318. Even if the fixation device engages the heart tissue, the medical practitioner can disengage the fixation device from the heart, and move the IMD lead to another location and reengage the fixation device with the heart tissue. Typically, this process of mapping, positioning the lead electrode in contact with the heart tissue, electrically stimulating the heart tissue, and possibly performing the cardiac cycle length variability analysis will be repeated until the medical practitioner is satisfied that the lead electrode is co-located with the driver, as shown in the exemplary algorithm 338 illustrated in FIG. 17.

In the exemplary algorithm 338, after the algorithm starts at step 340, a mapping electrode 98 that is part of a mapping catheter 94 is used to sense a signal that is emitted from a location within the heart 24 at step 342. At step 344, the signal is communicated from the mapping electrode to a computer 14, which is coupled to the mapping electrode. At step 346, the computer is used to calculate a standard deviation of cycle length value for the signal. Next, at step 348, the standard deviation of cycle length value is compared to other standard deviation of cycle length values that previously have been calculated by the computer for signals emitted from other locations within the heart.

At step 350, the approximate location of the fibrillation driver is determined based on the comparison of the standard deviation of cycle length values. Next, at step 352, the user 32 positions the IMD lead 266 so the lead electrode 268 is co-located with the approximate location of the fibrillation driver. At step 354, stimulation energy is applied to the heart 24 via the lead electrode, and the user observes the heart's response. Next, at step 356, it is determined if the lead electrode is co-located with the fibrillation driver. If the lead electrode is co-located with the fibrillation driver, then, at step 358, the user couples the IMD lead to the heart, and the algorithm 338 ends at step 360. If the lead electrode is not co-located with the fibrillation driver, then the steps of sensing the signal with the mapping electrode 98, calculating the standard deviation of cycle length value for the signal, comparing the standard deviation of cycle length values, determining the approximate location of the fibrillation driver, co-locating the lead electrode with the approximate location, and applying the stimulation energy to the heart via the lead electrode are repeated until the lead electrode is co-located with the fibrillation driver.

Referring again to FIGS. 13-16, after the IMD lead 266 is positioned securely in a desired location, the proximal end 312 of the IMD lead is decoupled from the interface device 332 or the diagnostic device 336, the guide wire 322 is removed from the IMD lead, and the lead connector 314 is coupled to the IMD's connector assembly 304. Finally, the medical practitioner 32 creates a pocket 362 beneath the patient's skin 364 in the upper portion 366 of the patient's chest 326 to hold the IMD 270, the IMD is implanted within the pocket, and the medical practitioner sutures the pocket closed.

In other embodiments, the IMD lead 266 is not inserted into a heart chamber 82, 84, 116 and/or 118 via the patient's venous system 66. Rather, the IMD lead is coupled to the heart 24 in an external manner. In such a case, the IMD lead is inserted into the patient's chest cavity 368 through a hole (not shown) in the pericardium (not shown). The lead electrode 268 is secured to a location in the heart's epicardial tissue 76 (see FIG. 13) after the desired location is determined, for example, using a mapping catheter 94, which is inserted into the heart via the patient's venous system (endocardial mapping), as previously mentioned, or using a mapping catheter that externally is positioned in contact with the patient's heart after being inserted into the patient's chest cavity through the hole in the pericardium (epicardial mapping), in combination with the cardiac cycle length variability analysis. Thus, the IMD lead can be secured to the outside surface of the heart.

In other embodiments, referring also to FIG. 4, the IMD lead 266 is inserted into the left atrium 86 from the right atrium 82 through a hole 88 that previously has been punched through the septum 90. Typically, the IMD lead is inserted into the left atrium after a mapping procedure (previously discussed in reference to the ablation process) is completed for the left atrium. Accordingly, an IMD lead can be installed in the left atrium so that the IMD lead can be used in therapies to counteract the effects of an AF driver in the left atrium. Thus, the present invention can be used for locating the position of an IMD lead in either the left atrium or the right atrium.

Figure 18:
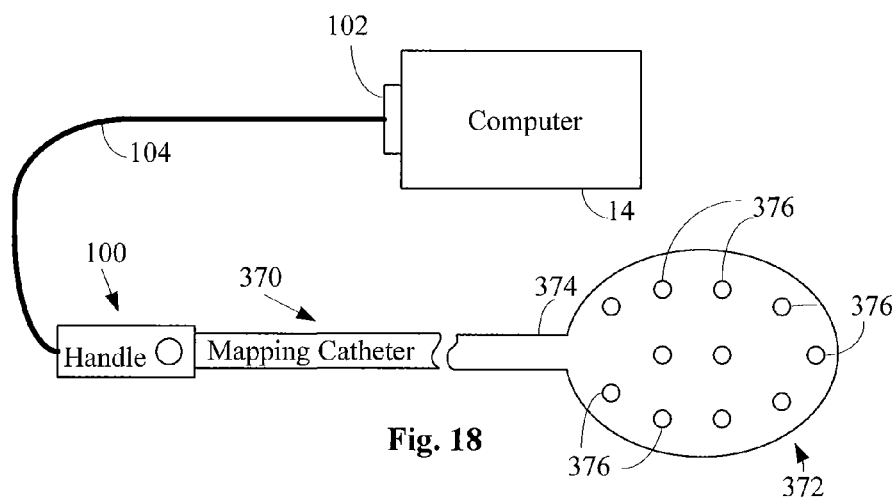
FIG. 18 is a simplified block diagram of a mapping system that includes a basket-type mapping catheter according to an embodiment of the present invention.

Embodiments of the present invention also can be used to treat ventricular fibrillation ("VF"), which is condition characterized by a lack of coordinated contraction of the muscles of the ventricles 116 and 118, and which typically results in heart stoppage. Similar to AF, VF can result from a driver, i.e., a VF driver, that is located in a ventricle. Referring additionally to FIG. 18, in these embodiments, a basket-type mapping catheter 370, also referred to as a balloon-type mapping catheter, typically is used to map the interior of a ventricle, either the right ventricle 116 or the left ventricle 118, during an EP mapping procedure. An example basket-type mapping catheter is the non-contact, multi-electrode array that is included in the ENSITE ARRAY MAPPING SYSTEM from St. Jude Medical of St. Paul, Minn. The basket-type mapping catheter is inserted into the heart 24 via the patient's venous system 66, as previously described. The basket-type mapping catheter includes a basket or balloon 372 at its distal end 374, which is configured to be expanded within the ventricle without making contact with the endocardium 74 within the ventricle. The basket includes a plurality of electrodes 376, which are used for mapping purposes. Referring again to FIG. 4, when mapping the left ventricle, the basket-type mapping catheter can be inserted into the left ventricle from the right ventricle via a hole 378 that is punched through the septum 90, or the basket-type mapping catheter can be inserted into the left ventricle via the patient's carotid artery (not shown) or femoral artery (not shown).

During the mapping procedure of the patient's ventricle(s) 116 and 118, a VF event is induced in the patient's heart 24, and during the VF event, the plurality of electrodes 376 in the basket 372 simultaneously collect electrical potential readings from the interior surface 74 of the ventricle. Knowing the distance between each of the plurality of electrodes and the interior surface of the ventricle, a map of the surface potential for the ventricle can be generated. After the data is collected using the basket-type mapping catheter 370, the patient 40 is cardioverted and brought back to a stable condition. Basket-type mapping catheters can be used to map an atrium 82 or 86 as well as a ventricle. In other embodiments, rather than using a basket-type mapping catheter, a regular mapping catheter 94 can be inserted into the patient through a hole (not shown) in the pericardium (not shown) and the heart can be epicardially mapped.

After the mapping procedure, the data is communicated to the computer 14, which is coupled to the mapping catheter 94 and 370, the medical practitioner 32 will review the data that is presented on the user output device 62, and the medical practitioner will determine where the ablation catheter 12 should apply ablation energy in the ventricle 116 and 118, or where the lead electrode 268 should be secured within the ventricle. The ablation catheter or the IMD lead 266 can be inserted into the right ventricle 116, as shown in FIGS. 2 and 15, or inserted into the left ventricle 118 via the hole 378 that was created in the septum 90 from the right ventricle 116, or via one of the patient's arteries, e.g., the carotid artery (not shown) or the femoral artery (not shown). Also, the ablation catheter can be inserted into the patient 40 through a hole (not shown) in the pericardium (not shown) and can be used to ablate the epicardium 76. In addition, rather than installing the IMD lead into the right or left ventricle, the IMD lead can be coupled to the epicardium of the ventricle. In which case, the IMD lead is inserted into the patient through the hole (not shown) in the pericardium (not shown).

Each of the IMD leads 266 is inserted and installed in the patient 40 separately. Thus, for an IMD 270 having three IMD leads, the medical practitioner 32 would perform the mapping procedure three times (once for each IMD lead) and perform the IMD lead installation procedure three times (once for each IMD lead). The cardiac cycle length variability analysis according to the present invention can be used during the installation of each of the IMD leads.

Advantageously, the cardiac cycle length variability analysis according to the present invention provides the medical practitioner 32 with a quick determination of the location of a driver within a patient's heart 24 during the mapping procedure that is performed before an IMD lead 266 is installed. Thus, the cardiac cycle length variability analysis reduces the amount of time spent performing the mapping procedure and the overall surgical time for the patient 40.

Also, because the cardiac cycle length variability analysis results in an accurate determination of the driver's location, the lead electrode 268 can be co-located with the driver, and thus, reduce inefficiencies that occur when a lead electrode is positioned in a location apart from the driver's location. For example, less energy will be required from the IMD 270 during stimulation therapy when the lead electrode is co-located with the driver. Another advantage that is associated with the present invention is that the cardiac cycle length variability analysis technique can be implemented using currently available ablation systems 10 and/or IMDs.

The foregoing detailed description of the present invention is provided for purposes of illustration, and it is not intended to be exhaustive or to limit the invention to the particular embodiments disclosed. The embodiments may provide different capabilities and benefits, depending on the configuration used to implement the key features of the invention. Accordingly, the scope of the invention is defined only by the following claims.

What is claimed is:

1. A system that is configured to approximate a location of a fibrillation driver within a heart, the system comprising:
   a. a plurality of electrodes configured to sense, at each of a respective location in the heart, a signal comprising a plurality of cardiac cycles each having a corresponding cardiac cycle length; and
   b. a computer that is coupled to the electrodes and configured to:
      calculate, for each of a plurality of the locations, a plurality of cardiac cycle length values for the signal sensed at the location and a standard deviation of the plurality of calculated cardiac cycle length values for the signal sensed at the location using only the plurality of calculated cardiac cycle length values calculated for that location,
      directly compare each of the respective calculated standard deviations to each of the other respective calculated standard deviations to determine the smallest standard deviation, and
      identify the location with the smallest standard deviation of cardiac cycle length values as the location closest to the fibrillation driver.

2. The system according to claim 1, wherein the computer is configured to notify the user of the location in the heart that emitted the signal having the smallest standard deviation of cardiac cycle length values.

3. The system according to claim 1, wherein the computer includes a user output device that is configured to display data for the signal having the smallest standard deviation of cardiac cycle length values, the data selected from the group consisting of the standard deviation of cycle length value, a mean cycle length value for the signal, the signal in the form of an electrogram, and a Fast Fourier Transformation of the signal.

4. The system according to claim 3, wherein the user output device is further configured to display the data in color.

5. The system according to claim 1, wherein:
   a. the computer includes a computer-readable medium; and
   b. the computer is configured to store the signals sensed by the electrodes in the computer-readable medium.

6. The system according to claim 1, wherein:
   the computer is configured to calculate a Fast Fourier Transformation (FFT) of each of the signals; compare the plurality of FFTs; select the one of the plurality of FFTs that has one or more of the following characteristics: single frequency peak and the highest value of peak frequency; and determine a location in the heart corresponding to the selected FFT.

7. The system according to claim 1, wherein:
   a. the signals are selected from the group consisting of atrial signals and ventricular signals;

b. the fibrillation driver is selected from the group consisting of an atrial fibrillation driver and a ventricular fibrillation driver; and
c. the fibrillation driver is located within a portion of the heart selected from the group consisting of a right atrium, a left atrium, a right ventricle, and a left ventricle.

8. The system according to claim 1, wherein:
a. the plurality of electrodes is included as part of a device selected from the group consisting of a mapping catheter, an ablation catheter, and an implantable medical device lead;
b. the device has a distal end;
c. the plurality of electrodes is located at the distal end;
d. the heart is located within a patient's body; and
e. the distal end is configured to be inserted into the patient's body.

9. A method for determining an approximate location of a fibrillation driver within a heart using a plurality of electrodes that are coupled to a computer, the method comprising:
a. using the electrodes to sense, at each of a respective location in the heart, a signal comprising a plurality of cardiac cycles each having a corresponding cardiac cycle length;
b. communicating the signals from the electrodes to the computer;
c. using the computer to calculate, for each of a plurality of the locations, a plurality of cardiac cycle length values for the signal sensed at the location and a standard deviation of the plurality of calculated cardiac cycle length values for the signal sensed at the location using only the plurality of calculated cardiac cycle length values calculated for that location;
d. directly comparing each of the respective calculated standard deviations to each of the other respective calculated standard deviations to determine the smallest standard deviation; and
e. identifying the location with the smallest standard deviation of cardiac cycle length values as the approximate location of the fibrillation driver within the heart.

10. The method according to claim 9, further comprising: using the computer to calculate a Fast Fourier Transformation (FFT) of each of the signals; compare the plurality of FFTs; select the one of the plurality of FFTs that has one or more of the following characteristics: single frequency peak and the highest value of peak frequency; and determine a location in the heart corresponding to the selected FFT.

11. The method according to claim 9, wherein the electrode is included as part of a mapping catheter and the approximate location of the fibrillation device is determined as part of an effort to ablate the fibrillation driver using an ablation catheter having a distal end that is configured to emit ablation energy into the heart, the method further comprising:
a. co-locating the distal end of the ablation catheter with the approximate location of the fibrillation driver;
b. emitting ablation energy from the distal end of the ablation catheter in an effort to destroy the fibrillation driver; and
c. determining if the fibrillation driver was destroyed;
d. wherein if the fibrillation driver was not destroyed after the emission of the ablation energy, repeating the steps of claim 9 and steps a-c of this claim.

12. The method according to claim 9, wherein the electrode is a mapping electrode that is included as part of a mapping catheter and the approximate location of the fibrillation driver is determined as part of an effort to install an implantable medical device lead having a lead electrode in the heart, the method further comprising:
a. positioning the implantable medical device lead so the lead electrode is co-located with the approximate location of the fibrillation driver; and
b. determining if the lead electrode is co-located with the fibrillation driver by applying stimulation energy to the heart via the lead electrode and observing a response of the heart.

13. The method according to claim 12, further comprising coupling the implantable medical device lead to a lining of the heart selected from the group consisting of an endocardial lining and an epicardial lining after it determining that the lead electrode is co-located with the fibrillation driver.

14. A system for determining an approximate location of a fibrillation driver within a heart, the system comprising:
a. means for sensing, at each of a respective location in the heart, a signal comprising a plurality of cardiac cycles each having a corresponding cardiac cycle length;
b. means for calculating, for each of a plurality of the locations, a plurality of cardiac cycle length values for the signal sensed at the location and a standard deviation of the plurality of calculated cardiac cycle length values for the signal sensed at the location using only the plurality of calculated cardiac cycle length values calculated for that location;
c. means for directly comparing each of the respective calculated standard deviations to each of the other respective calculated standard deviations to determine the smallest standard deviation; and
d. means identifying the location with the smallest standard deviation of cardiac cycle length values as the approximate location of the fibrillation driver within the heart.

* * * * *